United States Patent
Allen et al.

(10) Patent No.: US 9,872,640 B2
(45) Date of Patent: Jan. 23, 2018

(54) SYSTEMS, METHODS, AND DEVICES FOR CHARACTERIZING EAR CANAL ACOUSTIC IMPEDANCE, ADMITTANCE, AND REFLECTANCE BY POLE-ZERO FITTING

(71) Applicant: Mimosa Acoustics, Inc., Champaign, IL (US)

(72) Inventors: Jont B Allen, Mahomet, IL (US); Sarah Robinson, Urbana, IL (US)

(73) Assignee: Mimosa Acoustics, Inc., Champaign, IL (US)

( * ) Notice: Subject to any disclaimer, the term of this patent is extended or adjusted under 35 U.S.C. 154(b) by 252 days.

(21) Appl. No.: 14/222,508

(22) Filed: Mar. 21, 2014

(65) Prior Publication Data

US 2015/0265189 A1   Sep. 24, 2015

(51) Int. Cl.
*A61B 5/12*   (2006.01)

(52) U.S. Cl.
CPC .................... *A61B 5/126* (2013.01)

(58) Field of Classification Search
CPC ........... A61B 5/12; A61B 5/121; A61B 5/125; A61B 5/126; A61B 5/6817
See application file for complete search history.

(56) References Cited

U.S. PATENT DOCUMENTS

| | | | | |
|---|---|---|---|---|
| 3,496,479 A * | 2/1970 | MacPherson | .......... | H03H 19/00 327/45 |
| 2003/0144603 A1* | 7/2003 | Zoth | ....................... | A61B 5/121 600/559 |

OTHER PUBLICATIONS

Voss, S. & Allen, J. (1994). Measurement of acoustic impedance and reflectance in the human ear canal. Journal of the Acoustical Society of America, 95(1), 372-384.*
Puria, S. & Allen, J. (1998). Measurements and model of the cat middle ear: Evidence of tympanic membrane acoustic delay. Journal of the Acoustical Society of America, 104(6), 3463-3481.*
Gustaysen, B. & Semlyen, A. (1999). Rational Approximation of Frequency Domain Responses by Vector Fitting. IEEE Transactions on Power Delivery, 14(3), 1052-1061.*

(Continued)

*Primary Examiner* — Michael C Stout
*Assistant Examiner* — Nicholas E Kolderman
(74) *Attorney, Agent, or Firm* — Invention Mine LLC

(57) ABSTRACT

Embodiments for characterizing ear canal acoustic impedance and reflectance by pole-zero fitting are disclosed. Embodiments include transmitting an acoustic signal into an ear canal by a transducer having an acoustic source pressure. Further embodiments, measure complex cavity pressure, $P(f)$, response based on the transmitted acoustic signal reflected by eardrum using an acoustic measurement device. Additional, such embodiments, calculate complex acoustic reflectance (CAR) based on the $P(f)$. Other embodiments determine number of poles and zeroes of CAR pole-zero model to reduce residual error between the CAR pole-zero model and CAR data stored in memory within a threshold. Also, embodiments verify the residual error of CAR pole-zero model compared to the CAR data is within the threshold. Further, embodiments factor the CAR pole-zero model into an all pass component and a minimum phase component. Additional embodiments determine ear drum impedance by removing the all phase component of the CAR pole-zero model.

7 Claims, 13 Drawing Sheets

(56) References Cited

OTHER PUBLICATIONS

Allen, J.B., et al. 2005. "Evaluation of human middle ear function via an acoustic power assessment." Journal of Rehabilitation Research & Development 42, pp. 63-78.
Campbell, G.A. 1922. "Physical theory of the electric wave filter." Bell System Technical Journal 1, pp. 1-32.
Claerbout, J. 1985. "Imaging the Earth's Interior." Blackwell Scientific, Palo Alto, CA, pp. 287-289.
Fletcher, H. 1925. "Useful numerical constants of speech and hearing." Bell System Technical Journal IV, pp. 375-386.
Lundberg, K.H., et al. 2007. "Initial conditions, generalized functions, and the Laplace transform: troubles at the origin." IEEE Control Systems Magazine 27, pp. 22-35.
Nakajima, H.H., et al. 2012. "Comparison of ear-canal reflectance and umbo velocity in patients with conductive hearing loss: a preliminary study." Ear and Hearing 33, pp. 35-43.
Parent, P., et al. 2010. "Time-domain 'wave' model of the human tympanic membrane." Hearing Research 263, pp. 152-167.
Rasetshwane, D.M., et al. 2012. "Reflectance of acoustic horns and solution of the inverse problem." The Journal of the Acoustical Society of America 131, pp. 1863-1873.
Recio-Spinoso, A., et al. 2011. "Basilar-membrane responses to broadband noise modeled using linear filters with rational transfer functions." IEEE Transactions on Biomedical Engineering 58, pp. 1456-1465.
Rosowski, J.J., et al. 2003. "Diagnostic utility of laser-Doppler vibrometry in conductive hearing loss with normal tympanic membrane." Otology & Neurotology 24, pp. 165-175.
Rosowski, J.J., et al. 2012. "Ear-canal reflectance, umbo velocity, and tympanometry in normal-hearing adults." Ear and Hearing 33, pp. 19-34.
Rosowski, J.J., et al. 2008. "Clinical utility of laser-Doppler vibrometer measurements in live normal and pathologic human ears." Ear and Hearing 29, pp. 3-19.
Scheperle, R.A., et al. 2008. "Influence of in situ, sound-level calibration on distortion-product optoacoustic emission variability." The Journal of the Acoustical Society of America 124, pp. 288-300.
Voss, S.E., et al. 2012. "Effects of middle-ear disorders on power reflectance measured in cadaveric ear canals." Ear and Hearing 33, pp. 195-208.
Keefe, D.H., et al. 1992. "Method to measure acoustic impedance and reflection coefficient." The Journal of the Acoustical Society of America 91, pp. 470-485.
Van Valkenburg, M.E. 1964. "Modern Network Synthesis." John Weily & Sons, Inc., New Work, NY. Ch. 1 p. 16-19, 22-23, Ch.3 p. 64-65, Ch.4 p. 96-97, Ch.8 p. 196-199, Ch.12 p. 350-351.
Voss, S.E., et al. 2000. "Acoustic responses of the human middle ear." Hearing Research 150, pp. 43-69.
Withnell, R.H., Jeng, P.S, Waldvogel, K., Morgenstein, K., Allen, J.B. (2009) An in-situ calibration for hearing thresholds. Journal of the Acoustical Society of America, 125, 1605-1611.
Zwislocki, J. 1962. "Analysis of the middle-ear function. Part I: input impedance." The Journal of the Acoustical Society of America 34, pp. 1514-1523.
Farmer-Fedor, B.L, et al. 2002. "Acoustic intensity, impedance and reflection coefficient in the human ear canal." The Journal of the Acoustical Society of America 112, pp. 600-620.
Kringlebotn, M. 1988. "Network model for the human middle ear." Scandinavian Audiology 17, pp. 75-85.
Hunter, L.L., et al. 2010. "Wideband reflectance in newborns: normative regions and relationship to hearing-screening results." Ear and Hearing 31, pp. 599-610.
Feeney, M.P., et al. 2003. "Wideband energy reflectance measurements in adults with middle-ear disorders." Journal of Speech, Language, and Hearing Research 46, pp. 901-911.
Allen, J.B. 1986. "Measurement of Eardrum Acoustic Impedance." In: Allen, J.B., et al. "Peripheral Auditory Mechanisms". Springer-Verlag, New York, pp. 44-51.
Aibara, R., et al. 2001. "Human middle-ear sound transfer function and cochlear input impedance." Hearing Research 152, pp. 100-109.
Puria, S. & Allen, J. (1998). "Measurements and model of the cat middle ear: Evidence of tympanic membrane acoustic delay." Journal of the Acoustical Society of America, 104(6), pp. 3463-3481.
Robinson, Sarah R., et al. "Characterizing the ear canal acoustic impedance an reflectance by pole-zero fitting." Hearing Research 301 (2013), pp. 168-182.

* cited by examiner

SYSTEMS, METHODS, AND DEVICES FOR CHARACTERIZING EAR CANAL ACOUSTIC IMPEDANCE, ADMITTANCE, AND REFLECTANCE BY POLE-ZERO FITTING

BACKGROUND OF THE INVENTION

Acoustic reflectance measurements and their clinical applications have been the subject of many recent studies. These studies have shown that power reflectance, the magnitude squared of the complex acoustic reflectance (CAR), shows distinct and often systematic variations between pathological and normal middle ears (e.g. Feeney et al., 2003; Allen et al., 2005; Hunter et al., 2010). Studies by Voss et al. (2012) and Nakajima et al. (2012) have investigated the efficacy of reflectance measurements for differential diagnosis of middle ear pathology. Tympanometry and laser doppler vibrometry are the current standards for presurgical differentiation between ossicular fixation (Little to no movement of one or more of the three middle-ear bones), ossicular discontinuity (connection between 2 or more bones discontinues), and third window disorders (vibrations entering the ear canal and middle ear are then abnormally diverted through the superior semicircular canal and up into the intracranial space where they become absorbed instead of being registered as sound in the hearing center, the cochlea) (Rosowski et al., 2003). Tympanometry is an examination used to test the condition of the middle ear and mobility of the eardrum (tympanic membrane) and the conduction bones by creating variations of air pressure in the ear canal. Further, tympanometry is an objective test of middle-ear function. Tympanometry is not a hearing test, but rather a measure of energy transmission through the middle ear. Laser doppler vibrometry (LDV) is a scientific instrument that is used to make non-contact vibration measurements of a surface (e.g. an eardrum). The laser beam from the LDV is directed at the surface of interest, and the vibration amplitude and frequency are extracted from the Doppler shift of the reflected laser beam frequency due to the motion of the surface. Nakajima et al. concluded that analyzing the power reflectance performs as well as laser doppler vibrometry, both in combination with audiometry (e.g. airborne gap measurements), for differential diagnosis of middle ear disorders.

This is a valuable result, because CAR measurements can be performed using the United States Food and Drug Administration (FDA) 510(K) cleared HearID system (Mimosa Acoustics), which, as stated by Nakajima et al. (2012), costs an order of magnitude less than the laser Doppler vibrometer ($10; 000 vs. $100,000 USD) and requires less training to operate. In another recent study, Voss et al. (2012) systematically manipulated cadaver ears to isolate the effects of various pathologies with differing degrees of severity, and examined the CAR responses. They also concluded that power reflectance may be a strong supplement to audiometry for the diagnosis of certain pathologies of the middle ear.

CAR and impedance (where impedance is the inverse of admittance) are measured at ambient pressure by a probe (i.e. transducer) containing a microphone and loudspeaker, sealed in the ear canal via a foam tip. The probe is calibrated using a multi-cavity least squares procedure to find the Thévenin equivalent parameters of the acoustic source (as described in Allen, 1986). A stimulus (i.e. signal) is emitted by the probe, and the complex cavity pressure response is measured. From the calibration pressure responses, the acoustic impedance, reflectance, and related quantities (admittance, power reflectance, etc.) may be calculated. The CAR, denoted $\Gamma(\omega)$, is equal to the ratio of the reflected to incident wave pressure at the microphone, located in the ear canal, as a function of frequency ($\omega=2\pi f$). The magnitude squared of the reflectance, $|\Gamma(\omega)|^2$, represents the relative acoustic power reflected back to the ear canal from the middle and inner ears (e.g. from the ear drum). The power reflectance is related to conductive hearing functionality and is therefore relevant to clinical assessment of the middle ear (Allen et al., 2005). The complex acoustic impedance $Z(\omega)$ and reflectance $\Gamma(\omega)$, as functions of frequency, are related by $$\Gamma(\omega)=(Z(\omega)/r_0-1)/((Z(\omega))/r_{0+}1) \qquad (1)$$

$r_0=\rho c/A$ is the estimated surge resistance, $\rho$ is the density of air, c is the speed of sound, and A is the area of the ear canal. The 'surge' impedance (Campbell) is defined as the amplitude of the $\delta(t)$ component of the time-domain impedance; because it is a real constant, it is denoted as a resistance. It follows that the reflectance is strictly causal (i.e. zero at $t=0$) (Claerbout, 1985).

The clinical utility of CAR depends on its capacity to discern normal from pathological results, which requires a method for comparing measurements across ears. Direct comparison of CAR is complicated because the residual ear canal dimensions between the probe tip and tympanic membrane (TM) vary across subjects. This uncertainty has a large effect on the reflectance phase and the complex acoustic impedance. The residual ear canal is frequently modeled as a rigid-walled tube of uniform area A and length L, having a volume A*L.

Under this assumption, the relationship between the CAR at the probe and at the TM becomes $$\Gamma(\omega)=\Gamma_{TM}(\omega)e^{-(\rho L/c)\omega} \qquad (2)$$

In many cases this is not a realistic model, particularly because the residual ear canal area $A(x)$ varies with distance x (Farmer-Fedor and Rabbitt, 2002). Equation (2) represents a special case of a uniform (constant $A(x)$), lossless canal; a nonuniform, lossless canal would have a more complicated phase dependence on frequency. However, consideration of the CAR magnitude (or the power reflectance $|\Gamma(\omega)|^2$) is highly effective because even when $A(x)$ is nonuniform, the ear canal may be reasonably approximated as lossless, in which case $$|\Gamma(\omega)|=|\Gamma_{TM}(\omega)| \qquad (3)$$

Eliminating the variation due to the residual ear canal length (or volume) by using the CAR magnitude or power reflectance allows for comparison across measurements with unknown residual canal dimensions. Thus, the magnitude reflectance is the current diagnostic standard using CAR measurements. The relationship in Eq. (3) was experimentally verified by Voss et al. (2008).

While uncertainty in the residual ear canal length/volume significantly confounds phase information associated with the eardrum and ossicles, taking the magnitude of the CAR eliminates this relevant information entirely. It follows that a holistic analysis of the CAR data could be more powerful and generalizable if the canal effect were accounted for in a rigorous manner, without eliminating the phase data ($Y_{TM}(\omega)$). The pending disclosure describes such embodiments of systems, methods, and devices for concise parametric characterization of CAR measurements, thereby determining the effect of the residual ear canal on the CAR, the ear drum impedance with the ultimate goal of improving differential diagnosis of middle ear pathology. This is accomplished by fitting poles and zeros to the CAR data.

Accordingly, there is a need for systems, methods, and devices for characterizing ear canal acoustic impedance and reflectance by pole-zero fitting. The pending disclosure incorporates by reference "Characterizing the ear canal acoustic impedance and reflectance by pole-zero fitting" by Sarah R. Robinson, Cac T. Nguyen, and Jont B. Allen, Hearing Research 301 (2013) 168-182. The following reference are incorporated by reference in their entireties:

Aibara, R., Welsh, J. T., Puria, S., Goode, R. L., 2001. Human middle-ear sound transfer function and cochlear input impedance. Hearing Research 152, 100-109; Allen, J. B., 1986. Measurement of Eardrum Acoustic Impedance. In: Allen, J. B., Hall, J. L., Hubbard, A., Neely, S. T., Tubis, A. (Eds.), Peripheral Auditory Mechanisms. Springer-Verlag, New York, pp. 44-51; Allen, J. B., Jeng, P. S., Levitt, H., 2005. Evaluation of human middle ear function via an acoustic power assessment. Journal of Rehabilitation Research & Development 42, 63-78; Brune, O., 1931. Synthesis of a finite two-terminal network whose driving-point impedance is a prescribed function of frequency. Journal of Mathematical Physics 10, 191-236; Campbell, G. A., 1922. Physical theory of the electric wave filter. Bell System Technical Journal 1, 1-32; Claerbout, J., 1985. Imaging the Earth's Interior. Blackwell Scientific, Palo Alto, Calif., pp. 287-289; Farmer-Fedor, B. L., Rabbitt, R. D., 2002. Acoustic intensity, impedance and reflection coefficient in the human ear canal. The Journal of the Acoustical Society of America 112, 600-620; Feeney, M. P., Grant, I. L., Marryott, L. P., 2003. Wideband energy reflectance measurements in adults with middle-ear disorders. Journal of Speech, Language, and Hearing Research 46, 901-911; Fletcher, H., 1925. Useful numerical constants of speech and hearing. Bell System Technical Journal IV, 375-386; Gustaysen, B., Semlyen, A., 1999. Rational approximation of frequency domain responses by vector fitting. IEEE Transactions on Power Delivery 14, 1052-1061; Hunter, L. L., Feeney, M. P., Lapsley Miller, J. A., Jeng, P. S., Bohning, S., 2010. Wideband reflectance in newborns: nonnative regions and relationship to hearing-screening results. Ear and Hearing 31, 599-610; Keefe, D. H., Ling, R., Bulen, J. C., 1992. Method to measure acoustic impedance and reflection coefficient. The Journal of the Acoustical Society of America 91, 470-485; Kringlebotn, M., 1988. Network model for the human middle ear. Scandinavian Audiology 17, 75-85; Lundberg, K. H., Miller, H. R., Trumper, R. L., 2007. Initial conditions, generalized functions, and the Laplace transform: troubles at the origin. IEEE Control Systems Magazine 27, 22-35; Nakajima, H. H., Pisano, D. V., Roosli, C., Hamade, M. A., Merchant, G. R., Mahfoud, L., Halpin, C. F., Rosowski, J. J., Merchant, S. N., 2012. Comparison of ear-canal reflectance and umbo velocity in patients with conductive hearing loss: a preliminary study. Ear and Hearing 33, 35-43; Parent, P., Allen, J. B., 2010. Time-domain "wave" model of the human tympanic membrane. Hearing Research 263, 152-167; Puria, S., Allen, J. B., 1998. Measurements and model of the cat middle ear: evidence of tympanic membrane acoustic delay. The Journal of the Acoustical Society of America 104, 3463-3481; Rasetshwane, D. M., Neely, S. T., Allen, J. B., Shera, C. A., 2012. Reflectance of acoustic horns and solution of the inverse problem. The Journal of the Acoustical Society of America 131, 1863-1873; Recio-Spinoso, A., Fan, Y., Ruggero, A., 2011. Basilar-membrane responses to broadband noise modeled using linear filters with rational transfer functions. IEEE Transactions on Biomedical Engineering 58, 1456-1465; Rosowski, J. J., Mehta, R. P., Merchant, S. N., 2003. Diagnostic utility of laser-doppler vibrometry in conductive hearing loss with normal tympanic membrane. Otology & Neurotology 24, 165-175; Rosowski, J. J., Nakajima, H. H., Hamade, M. A., Mahfoud, L., Merchant, G. R., Halpin, C. F., Merchant, S. N., 2012. Ear-canal reflectance, umbo velocity, and tympanometry in normal-hearing adults. Ear and Hearing 33, 19-34; Rosowski, J. J., Nakajima, H. H., Merchant, S. N., 2008. Clinical utility of laser-doppler vibrometer measurements in live normal and pathologic human ears. Ear and Hearing 29, 3-19; Scheperle, R. A., Neely, S. T., Kopun, J. G., Gorga, M. P., 2008. Influence of in situ, sound-level calibration on distortion-product otoacoustic emission variability. The Journal of the Acoustical Society of America 124, 288-300; Van Valkenburg, M. E., 1964. Modern Network Synthesis. John Weily & Sons, Inc., New York, N. Y.; Voss, S. E., Allen, J. B., 1994. Measurement of acoustic impedance and reflectance in the human ear canal. The Journal of the Acoustical Society of America 95, 372-384; Voss, S. E., Horton, N. J., Woodbury, R. R., Sheffield, K. N., 2008. Sources of variability in reflectance measurements on normal cadaver ears. Ear and Hearing 29, 651-665; Voss, S. E., Merchant, G. R., Horton, N. J., 2012. Effects of middle-ear disorders on power reflectance measured in cadaveric ear canals. Ear and Hearing 33, 195-208; Voss, S. E., Rosowski, J. J., Merchant, S. N., Peake, W. T., 2000. Acoustic responses of the human middle ear. Hearing Research 150, 43-69; Withnell, R. H., Jeng, P. S., Waldvogel, K., Morgenstein, K., Allen, J. B., 2009. An in situ calibration for hearing thresholds. The Journal of the Acoustical Society of America 125, 1605-1611; Zwislocki, J., 1962. Analysis of the middle-ear function. part I: input impedance. The Journal of the Acoustical Society of America 34, 1514-1523; Robinson, S. R., Nguyen, C. T., & Allen, J. B. (2013). Characterizing the ear canal acoustic impedance and reflectance by pole-zero fitting. Hearing Research, 301, 168-182.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
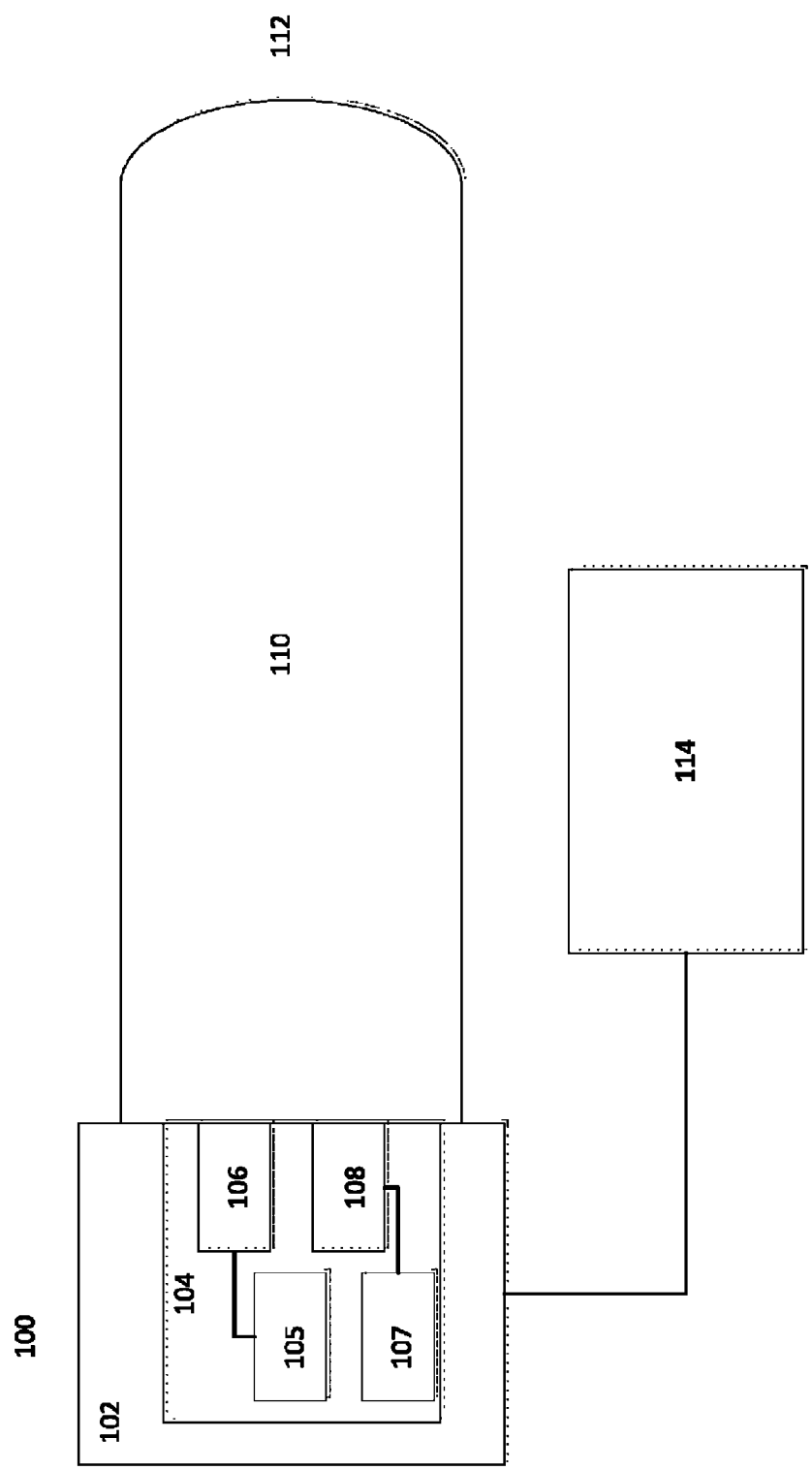
FIG. 1 is a block diagram of system for characterizing ear canal acoustic impedance and reflectance by pole-zero fitting, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

The illustrative embodiments described in the detailed description, drawings, and claims are not meant to be limiting. Other embodiments may be utilized, and other changes may be made, without departing from the scope of the subject matter presented herein. It will be readily understood that the aspects of the present disclosure, as generally described herein, and illustrated in the Figures, can be arranged, substituted, combined, separated, and designed in a wide variety of difference configurations, all of which are explicitly contemplated herein. Further, in the foregoing description, numerous details are set forth to further describe and explain one or more embodiments. These details include system configurations, block module diagrams, flowcharts (including transaction diagrams), and accompanying written description. While these details are helpful to explain one or more embodiments of the disclosure, those skilled in the art will understand that these specific details are not required in order to practice the embodiments.

As will be appreciated by one skilled in the art, aspects of the present disclosure may be embodied as an apparatus that incorporates some software components. Accordingly, some embodiments of the present disclosure, or portions thereof, may combine one or more hardware components such as microprocessors, microcontrollers, or digital sequential logic, etc., such as processor with one or more software components (e.g., program code, firmware, resident software, micro-code, etc.) stored in a tangible computer-readable memory device such as a tangible computer memory device, that in combination form a specifically configured apparatus that performs the functions as described herein. These combinations that form specially-programmed devices may be generally referred to herein as "modules". The software component portions of the modules may be written in any computer language and may be a portion of a monolithic code base, or may be developed in more discrete code portions such as is typical in object-oriented computer languages. In addition, the modules may be distributed across a plurality of computer platforms, servers, terminals, mobile devices and the like. A given module may even be implemented such that the described functions are performed by separate processors and/or computing hardware platforms.

The pending disclosure describes embodiments for systems, methods, and devices for characterizing ear canal acoustic impedance and reflectance by pole-zero fitting to determine ear drum impedance thereby assessing any middle ear pathologies from analyzing the ear drum impedance. Such embodiments include transmitting an acoustic signal into an ear canal by a transducer having an acoustic source pressure. The transducer is calibrated to generate a signal based on a pressure parameter of the acoustic source. Further, such embodiments, measure a complex cavity pressure, P(f), response based on the transmitted acoustic signal reflected by eardrum using a microphone and/or acoustic measurement device. In addition, such embodiment, calculate, by a computing device, a complex acoustic reflectance (CAR) based on the measured complex cavity pressure, P(f). The calculated CAR based on the measured complex cavity pressure comprises CAR measurement data stored in memory. Moreover, such embodiments determine, by the computing device, a number of poles and zeroes of a CAR pole-zero model to reduce residual error between the CAR pole-zero model and CAR measurement data stored in memory within a threshold. Also, such embodiments, verify, by the computing device, the residual error of CAR pole-zero model compared to the CAR measurement data is within the threshold. Further, such embodiments factor, by the computing device, the CAR pole-zero model into an all pass component and a minimum phase component. In addition, such embodiments determine, by the computing device, ear drum impedance by removing the all phase component of the CAR pole-zero model. Thus, the ear drum impedance may be analyzed to determine any middle ear pathologies. Note, $f=\omega/2\pi$.

FIG. 1 is a block diagram of system 100 for characterizing ear canal acoustic impedance and reflectance by pole-zero fitting, in accordance with some embodiments. The system 100 includes an acoustic device 102 coupled to an ear canal 110 having an ear drum (tympanic membrane) 112. The acoustic device 102 includes a transducer (i.e. probe) 104. Further, the transducer 104 includes a speaker 106 and microphone 108. In addition, the acoustic device 102 may be coupled to a computing device 114.

The transducer 104, having an acoustic source 105, may transmit an acoustic signal into the ear canal 110. Further, the transducer 104 is calibrated to generate a signal based on one or more parameters of the acoustic source 105 (e.g. Norton or Thevenin equivalent parameters). The acoustic source 105 may be a signal generator that generates one or more acoustic signals (e.g. chirps/tones) and may be coupled to the speaker 106 that transmits the acoustic signal(s) into the ear canal 110. Further, a microphone 108 receives acoustic signal(s) reflected by the ear drum 112. In addition, the transducer 104 may include an acoustic measurement device 107 couple to the microphone 108. The received reflected acoustic signal(s) are relayed from the microphone 108 to the acoustic measurement device 107 such that the acoustic measurement device measures a measure a complex cavity pressure, P(f), response based on the transmitted acoustic signal reflected by eardrum.

Moreover, the computing device 114 is coupled to the acoustic measurement device 107 and the computing device 114 receives the complex cavity pressure response from the acoustic measurement device 107. Such complex cavity pressure response may be referred to measurement data or raw data and may be stored in memory or a storage device coupled to the computing device 114. In addition, the computing device 114 and the acoustic measurement device 107 may couple over a wired or wireless link. Further, the computing device 114 calculates a complex acoustic reflectance (CAR) based on the measured complex cavity pressure. The complex acoustic reflectance (CAR) is based on a ratio of a reflected incident wave pressure to an incident wave pressure. The CAR data calculated from the measurement data or raw data of the measured complex cavity pressure response may be referred to as the CAR measurement data and may be stored in memory or a storage device coupled to the computing device 114.

In addition, the computing device 114 determines poles and zeroes of a CAR pole-zero model to reduce residual error between the CAR pole zero model and the CAR measurement data within a threshold. The computing device 114 may use a vector fitting procedure to determine the poles and zeroes of the complex acoustic reflectance. Further, the residual error threshold may be, for example, 3%, 5%, 10% or any threshold such that the CAR pole-zero model is considered reasonably close to the CAR measurement data.

The computing device 114 also verifies that the residual error of the CAR pole-zero model compared to the CAR measurement data is within the threshold. Further, the computing device 114 factors, using Weiner filtering, the CAR pole-zero model into an all pass component and a minimum phase component. In addition, the computing device 114 determines ear drum impedance by removing the all phase component of the CAR pole-zero model. Thus, the ear drum impedance may be analyzed to determine any middle ear pathologies.

Figure 2:
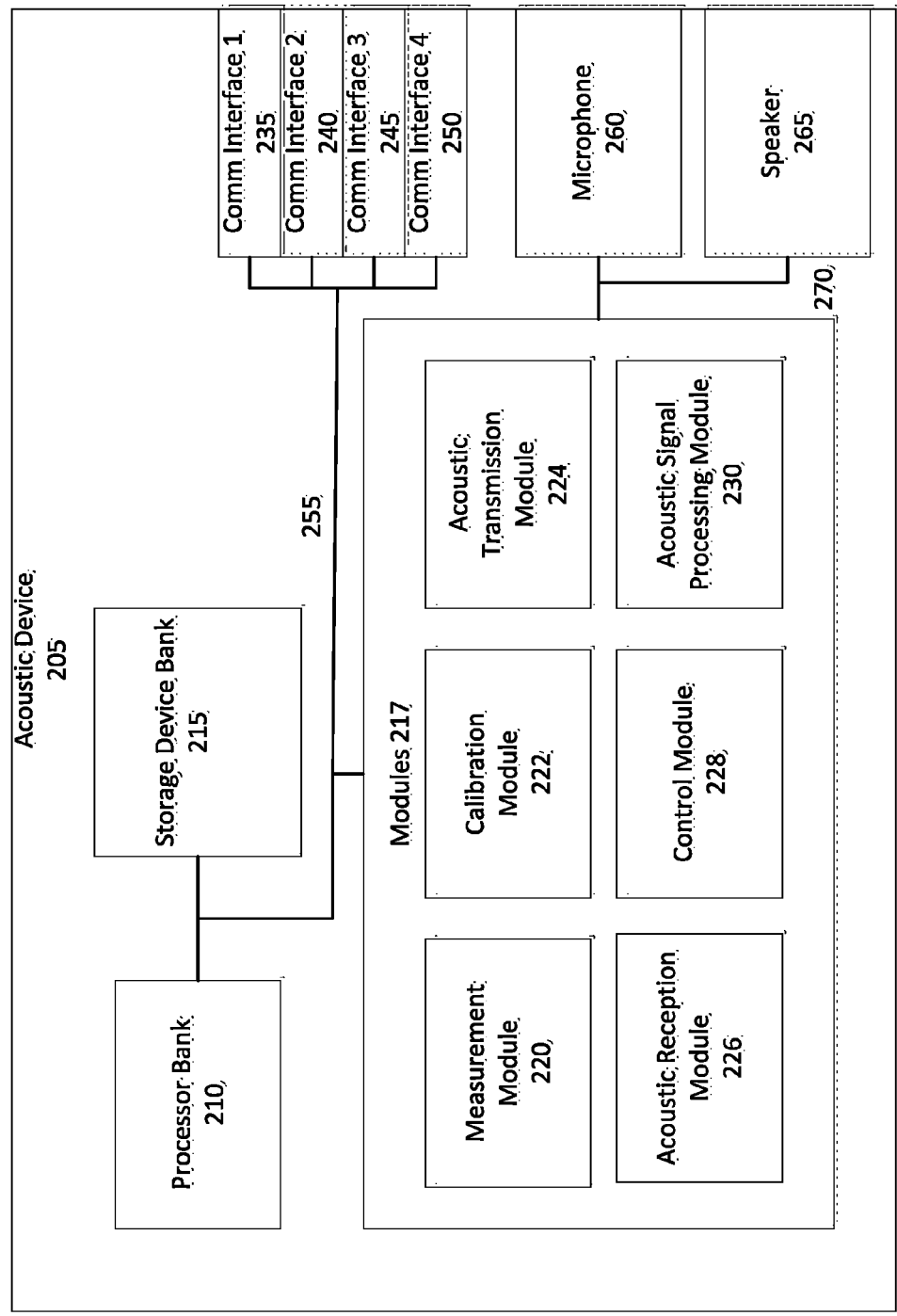
FIG. 2 is a block diagram of an acoustic device used in a system for characterizing ear canal acoustic impedance and reflectance by pole-zero fitting, in accordance with some embodiments.

Although the embodiment shows the computing device 114 to be coupled to acoustic device 102, other embodiments may include that the computing device 114 or functions of the computing device 114 described herein may be integrated into the acoustic device 102. FIG. 2 illustrates an embodiment that the functions of computing device 114 are integrated into an acoustic device. Alternatively, FIG. 3 describes an embodiment that a computing device is coupled to acoustic device 114 similar to the embodiment described and shown in FIG. 1.

FIG. 2 is a block diagram 200 of an acoustic device 205 used in a system for characterizing ear canal acoustic impedance and reflectance by pole-zero fitting, in accordance with some embodiments. Such embodiments of acoustic device 205 may be used in a system shown in FIG. 1. The acoustic device 205 may include several different components such as a processor bank 210, storage device bank 215, one or more software applications, which may be executed by a processor form specifically-configured module devices 217, and one or more communication interfaces (235-250). The processor bank 210 may include one or more processors that may be co-located with each other or may be located in different parts of the acoustic device 205. The storage device bank 215 may include one or more storage devices. Types of storage devices may include memory devices, electronic memory, optical memory, and removable storage media. The one or more modules 217 may include a measurement module 220, calibration module 222, acoustic transmission module 224, acoustic reception module 226, control module 228, and acoustic signal processing module 230. The modules 217 may be implemented by the one or more processors in the processor bank 210.

The acoustic transmission module 224 may include an acoustic source such as a signal generator that provides a signal to be transmitted by the speaker 265 into the ear canal. One embodiment, the acoustic transmission module 224 may provide chirps, single tones or multiple tones to the speaker 265 to transmit into the ear canal.

The calibration module 222 calibrates components of the acoustic device 205 based on Norton or Thevenin equivalent parameters of an acoustic source. Once calibrated, the speaker 265 can provide a calibrated signal to the ear canal.

The acoustic reception module 226 may receive an acoustic signal from the microphone 260. Such an acoustic signal may be a reflection of the transmitted signal provided by the acoustic transmission module 224 from an eardrum of a subject person. Such an acoustic signal may be provided to the acoustic signal processing module 230.

The acoustic processing module 230 may process a signal received from the ear canal by the microphone 260 and the acoustic reception module 226. Acoustic signal processing may include filtering, amplifying, reducing distortion, etc. of the received acoustic signal.

The measurement module 220 may receive the processed, received acoustic signal and measure or determine different components of the processed, received acoustic signal. Further, the measurement module 220 measures a complex cavity pressure, P(f), response based on the received acoustic signal reflected by eardrum. Such measured complex cavity pressure response may be referred to measurement data or raw data and may be stored in memory or a storage device 215. In addition, the measurement module 220 calculates a complex acoustic reflectance (CAR) based on the measured complex cavity pressure. The complex acoustic reflectance (CAR) is based on a ratio of a reflected incident wave pressure to an incident wave pressure. The CAR data calculated from the measurement data or raw data of the measured complex cavity pressure response may be referred to as the CAR measurement data and may be stored in memory or a storage device 215.

In addition, the measurement module 220 determines poles and zeroes of a CAR pole-zero model to reduce residual error between the CAR pole zero model and the CAR measurement data within a threshold. The measurement module 220 may use a vector fitting procedure to determine the poles and zeroes of the complex acoustic reflectance. Further, the residual error threshold may be, for example, 3%, 5%, 10% or any threshold such that the CAR pole-zero model is considered reasonably close to the CAR measurement data.

The measurement module also verifies that the residual error of the CAR pole-zero model compared to the CAR measurement data is within the threshold. Further, the measurement module 220 factors, using Weiner filtering, the CAR pole-zero model into an all pass component and a minimum phase component. In addition, the measurement module 220 determines ear drum impedance by removing the all phase component of the CAR pole-zero model. Thus, the ear drum impedance may be analyzed to determine any middle ear pathologies.

The control module 228 may implement functions that assist in performing certain tasks for the acoustic device 205 such as providing access to a communication network, executing an operating system, managing software drivers for peripheral components, and processing information. Further, control module 228 may implement software drivers for peripheral components, user interface computer programs, debugging and troubleshooting software tools.

Each of the communication interfaces (235-250) may be software or hardware associated in communicating to other devices. The communication interfaces (235-250) may be of different types that include a user interface, USB, Ethernet, WiFi, WiMax, wireless, optical, cellular, or any other communication interface coupled to a communication network.

An intra-device communication links 255 between the processor bank 210, storage device bank 215, modules 217, and communication interfaces (235-250) may be one of several types that include a bus or other communication mechanism.

Figure 3:
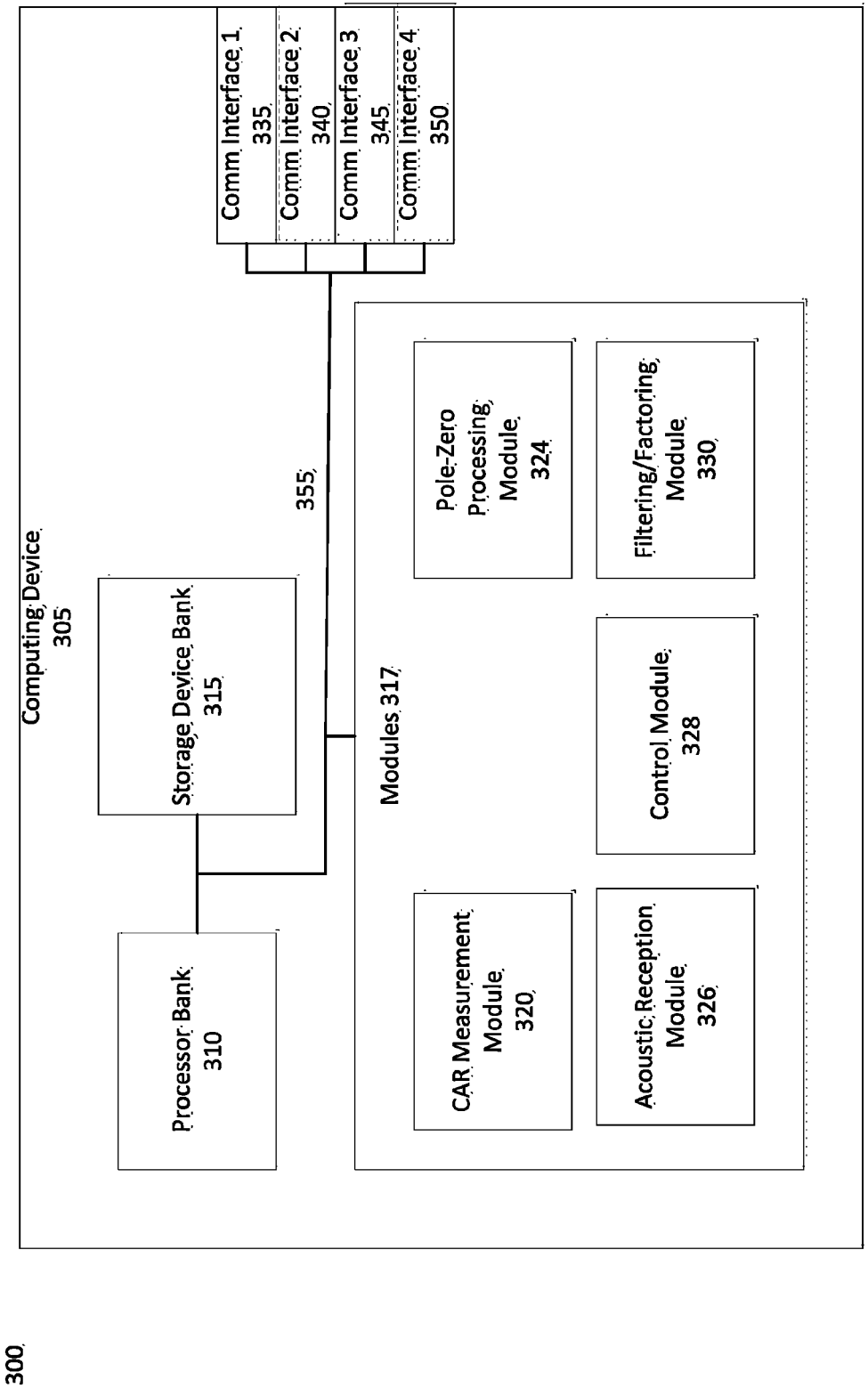
FIG. 3 is a block diagram of a computing device used in a system for characterizing ear canal acoustic impedance and reflectance by pole-zero fitting, in accordance with some embodiments.

FIG. 3 is a block diagram of a computing device 305 used in a system for characterizing ear canal acoustic impedance and reflectance by pole-zero fitting, in accordance with some embodiments. Embodiments of such a computing device 305 may be coupled to an acoustic device as shown in FIG. 1. The computing device 305 may include several different components such as a processor bank 310, storage device bank 315, one or more software applications, which may be executed by a processor form specifically-configured module devices 317, and one or more communication interfaces (335-350). The processor bank 310 may include one or more processors that may be co-located with each other or may be located in different parts of the computing device 305. The storage device bank 315 may include one or more storage devices. Types of storage devices may include memory devices, electronic memory, optical memory, and removable storage media. The one or more modules 317 may include a CAR measurement module 320, pole-zero processing module 324, acoustic reception module 326, control module 328, and filtering/factoring module 330. The modules 317 may be implemented by the one or more processors in the processor bank 310.

The acoustic reception module 326 may receive an acoustic signal from an acoustic device. Such an acoustic signal may be a reflection of the transmitted signal provided acoustic device from an eardrum of a subject person. Further, the received signal may be processed that includes include filtering, amplifying, reducing distortion, etc. of the received acoustic signal. Such a received acoustic signal may be provided to the CAR measurement module 320.

The CAR measurement module 320 may receive the processed, received acoustic signal and measure or determine different components of the processed, received acoustic signal. Further, the CAR measurement module 320 measures a complex cavity pressure, P(f), response based on the received acoustic signal reflected by eardrum. Such measured complex cavity pressure response may be referred to as measurement data or raw data and may be stored in memory or a storage device 315. In addition, the CAR measurement module 320 calculates a complex acoustic reflectance (CAR) based on the measured complex cavity pressure. The complex acoustic reflectance (CAR) is based on a ratio of a reflected incident wave pressure to an incident wave pressure. The CAR data calculated from the measurement data or raw data of the measured complex cavity pressure response may be referred to as the CAR measurement data and may be stored in memory or a storage device 315.

The pole-zero processing module 324 determines poles and zeroes of a CAR pole-zero model (based on the CAR measurement data) to reduce residual error between the CAR pole zero model and the CAR measurement data within a threshold. The pole-zero processing module 324 may use a vector fitting procedure to determine the poles and zeroes of the complex acoustic reflectance. Further, the residual error threshold may be, for example, 3%, 5%, 10% or any threshold such that the CAR pole-zero model is considered reasonably close to the CAR measurement data. The pole-zero processing module 324 also verifies that the residual error of the CAR pole-zero model compared to the CAR measurement data is within the threshold.

The filtering/factoring module 330 factors, using Weiner filtering, the CAR pole-zero model into an all pass component and a minimum phase component. In addition, the filtering/factoring module 330 determines ear drum impedance by removing the all phase component of the CAR pole-zero model. Thus, the ear drum impedance may be analyzed to determine any middle ear pathologies.

The control module 328 may implement functions that assist in performing certain tasks for the acoustic device 305 such as providing access to a communication network, executing an operating system, managing software drivers for peripheral components, and processing information. Further, control module 328 may implement software drivers for peripheral components, user interface computer programs, debugging and troubleshooting software tools.

Each of the communication interfaces (335-350) may be software or hardware associated in communicating to other devices. The communication interfaces (335-350) may be of different types that include a user interface, USB, Ethernet, WiFi, WiMax, wireless, optical, cellular, or any other communication interface coupled to a communication network.

An intra-device communication links 355 between the processor bank 310, storage device bank 315, modules 317, and communication interfaces (335-350) may be one of several types that include a bus or other communication mechanism.

Figure 4:
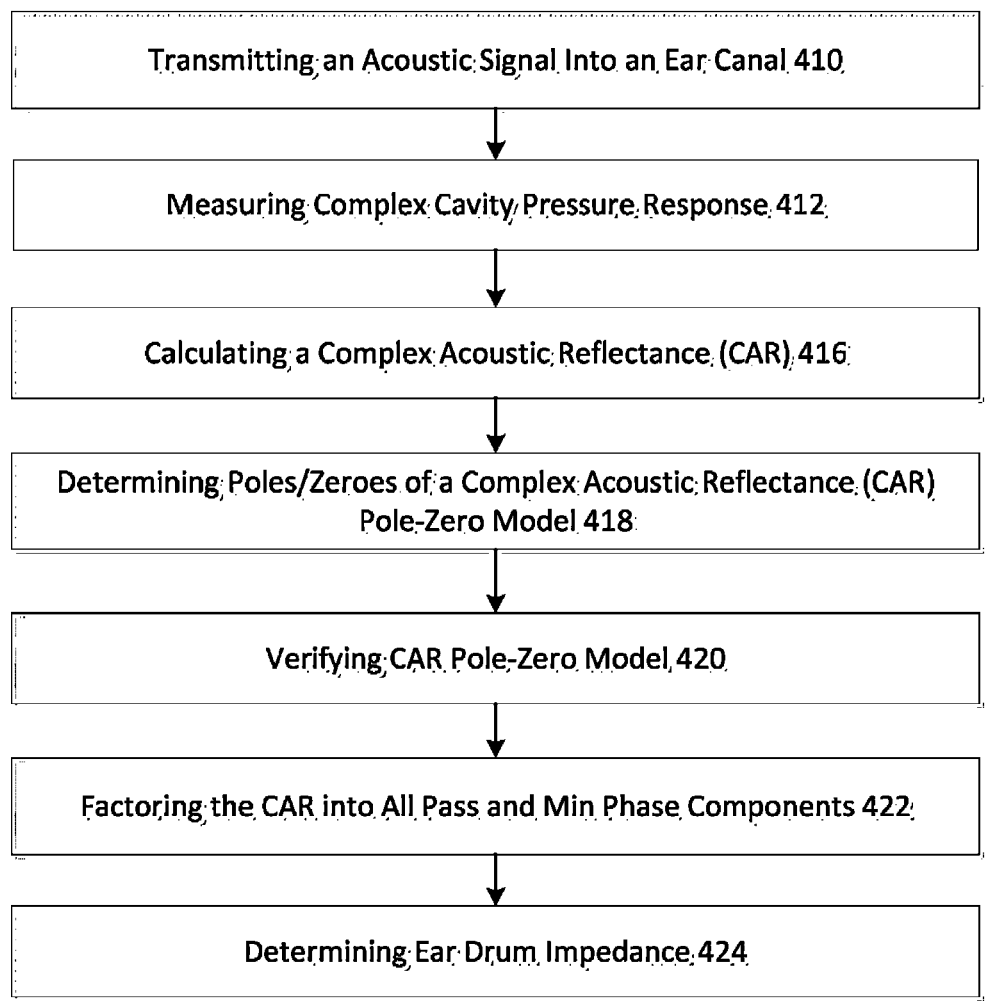
FIG. 4 is a flowchart of a method for characterizing ear canal acoustic impedance and reflectance by pole-zero fitting, in accordance with some embodiments.

FIG. 4 is a flowchart of a method 400 of for characterizing ear canal acoustic impedance and reflectance by pole-zero fitting, in accordance with some embodiments. The method 400 transmitting an acoustic signal into an ear canal by a transducer having an acoustic source pressure, as shown in block 410. The transducer is calibrated to generate a signal based on one or more parameters of the acoustic source. The parameters of the acoustic source may include the Norton equivalent parameters or the Thevenin equivalent parameters of the acoustic source. Further, the method 400 includes, measuring a complex cavity pressure, P(f), response based on the transmitted acoustic signal reflected by eardrum using a microphone and/or acoustic measurement device, as shown in block 412. Moreover, the method 400 includes calculating, a complex acoustic reflectance (CAR) based on the measured complex cavity pressure, P(f), as shown in block 416. The calculated CAR based on the measured complex cavity pressure comprises CAR measurement data stored in memory. The complex acoustic reflectance is based on a ratio of a reflected incident wave pressure to an incident wave pressure. Also, the method 400 includes determining by the computing device, a number of poles and zeroes of a CAR pole-zero model to reduce residual error between the CAR pole-zero model and CAR measurement data stored in memory within a threshold, as shown in block 418. A vector fitting procedure may be used to determine the poles and zeroes of the complex acoustic reflectance. The poles and zeros are determined to reduce the residual error and the measurement data stored in memory of the computing device within a threshold (e.g. 3%). Further the method 400 includes verifying, by the computing device, the residual error of CAR pole-zero model compared to the CAR measurement data is within the threshold, as shown in block 420. In addition, the method 400 includes factoring, by the computing device, the CAR pole-zero model into an all pass component and a minimum phase component, as shown in block 422. The computing device may use Weiner filtering to factor the complex acoustic reflectance into an all pass component and a minimum phase component. Moreover, the method 400 includes determining, by the computing device, ear drum impedance by removing the all phase component of the CAR pole-zero model, as shown in block 424. That is, the method 400 may also include calculating the ear drum impedance based on the minimum phase component of the CAR pole-zero model. Thus, the ear drum impedance may be analyzed to determine any middle ear pathologies.

FIGS. 5-13 and associated description describe the details of determining a number of poles and zeros of a CAR pole-zero model, verifying that the error of the CAR pole zero model is within a threshold, factoring a CAR pole-zero model into an all pass component and a minimum phase component as well as determining the ear drum impedance of the all phase component of the CAR pole-zero model to determine middle ear conditions and/or pathologies.

Figure 5:
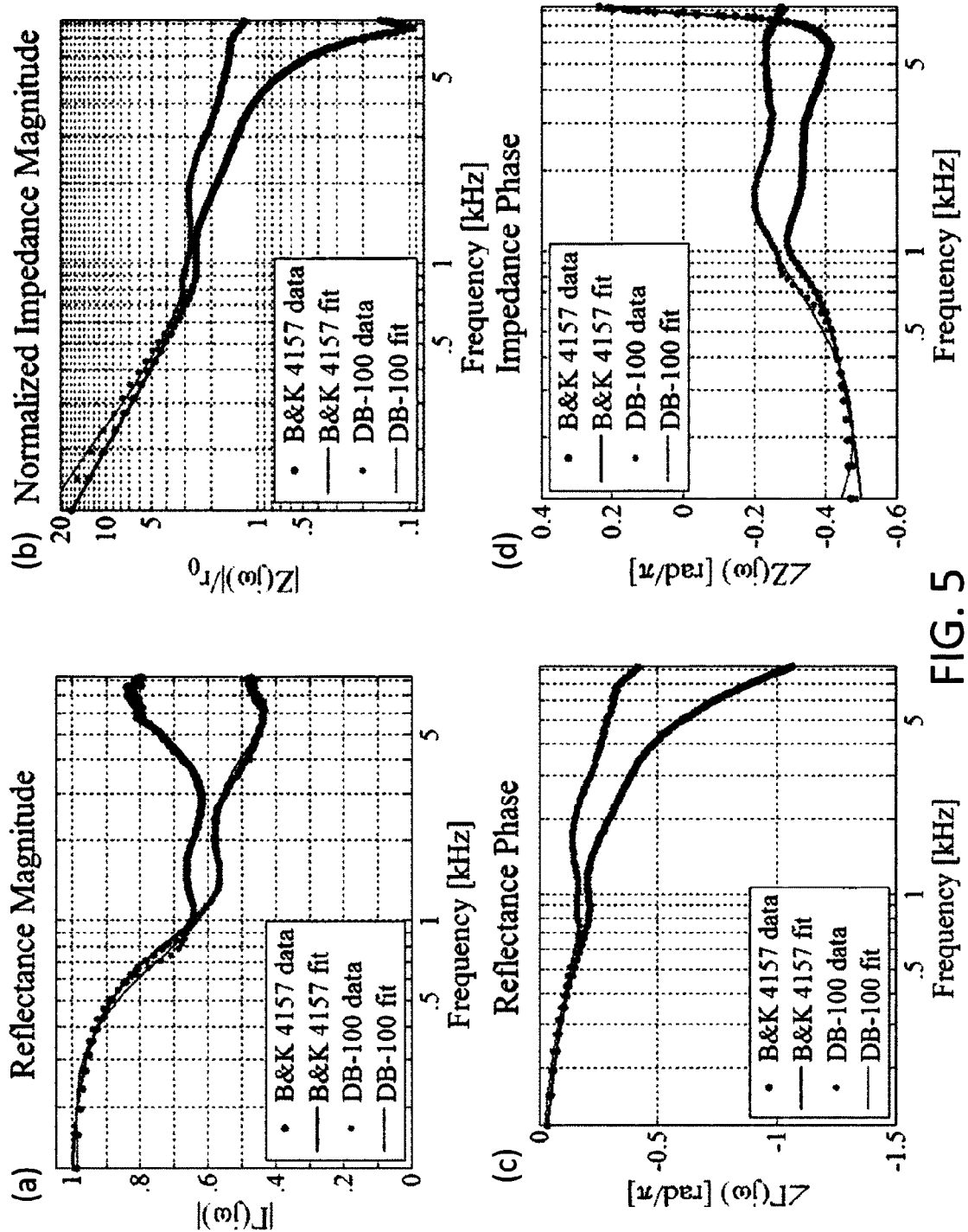
FIG. 5 are plots of example CAR measurement data and pole-zero fits of a corresponding CAR pole-zero model.

FIG. 5 are plots of example CAR measurement data and pole-zero fits of a corresponding CAR pole-zero model. In determining the CAR pole-zero model, poles and zeros may be expressed in terms of a rational polynomial fraction, as the roots of the denominator and numerator, respectively. Such a function may have the form $$\hat{F}(s) = \frac{(b_{Nz}s^{Nz} + b_{Nz-1}s^{Nz-1} + \ldots + b_1 s + b_0)}{(a_{Np}s^{Np} + a_{Np-1}s^{Np-1} + \ldots + a_1 s + a_0)} \quad (4)$$

$$= b_{Nz} \left[ \prod_{i=1}^{N_z} (s - z_i) \right] / \left[ \prod_{i=1}^{N_p} (s - p_i) \right]$$

where s is the complex angular frequency variable (s=σ+jω), $a_i$ and $b_i$ are the polynomial coefficients, $N_p$ is the number of poles, $N_z$ is the number of zeros, $p_i$ are the poles, and $z_i$ are the zeros (Van Valkenburg, 1964) and $\hat{F}(s)$ is the CAR measurement data calculated from the measured cavity pressure, P(f), response. In some embodiments, the relative order is constrained to $|N_z-N_p| \le 1$ by a vector fitting procedure as shown in Gustaysen and Semlyen (1999). Poles and zeros are a familiar concept regarding impedance considering Eq. (1), the reflectance must also have poles and zeros via a simple algebraic transformation. Thus, $\hat{F}(s)$ may be a fit to the impedance Z, the reflectance Γ, or some other simple algebraic transformation of the data.

Some example CAR measurement data (dots) and pole-zero fits (lines) are shown in FIG. 5 for two standard artificial ear simulators, the B&K 4157 (black) and the DB-100 (gray). These measurements are from Voss and Allen (1994). Each fit is performed on reflectance domain data (Γ(ω)) with $N_p=N_z=6$; the B&K 4157 fit has a RMS relative error of 1.7%, and the DB-100 fit has a RMS relative error of 2.9%. Reflectance and impedance magnitude vs. frequency (FIG. 5(a),(b)), and phase vs. frequency (FIG. 5(c),(d)), are shown for both couplers. The impedance is normalized by the estimated surge resistance, $r_0$. Effects of the residual simulator ear canals are particularly noticeable in the reflectance phase and normalized impedance magnitude. Considering the reflectance phase (FIG. 5(c)), the DB-100 has a much flatter phase across frequency than the B&K 4157, indicating less delay and thus a shorter residual ear canal (i.e. residual ear canal is the end of the probe to the ear drum). The normalized impedance magnitude of the B&K 4157 shows a high frequency notch, while the normalized impedance magnitude of the DB-100 does not. This deep notch is due to the ear canal 'standing wave' between the TM and the probe tip (Scheperle et al., 2008; Withnell et al., 2009). The absence of such a notch in the DB-100 impedance magnitude indicates a shorter distance between the probe tip and TM; however, such a notch may still exist, but at a higher frequency outside of the measured range. Finally, considering the impedance magnitude and phase, the B&K 4157 ear canal impedance becomes mass dominated at high frequencies (beyond the standing wave frequency) while the DB-100 impedance does not.

According to Voss and Allen (1994), the reflectance magnitude of the DB-100 ear simulator best resembles that of their ten human ear average below 4 [kHz], but the B&K 4157 is a better match to the average for frequencies up to 10 [kHz]. Considering FIG. 5(a), the B&K 4157 reflectance magnitude is close to one at low frequencies, has a broad minimum from about 1 to 4 [kHz], and rises again at high frequencies; this is also similar to the average results obtained by Rosowski et al. (2012), among others. However, the reflectance magnitude of the DB-100 does not share this high frequency behavior, instead continuing to decrease above 4 [kHz]. Thus, the B&K 4157 measurement is a better standard for comparison of complex pole-zero fits and to represent an average normal ear. It is important to note that while the average magnitude reflectance of normal middle ears has a broad, flat minimum from about 1 to 4 [kHz], individual ears have variable fine-structure minima and maxima in this range (Rosowski et al., 2012; Allen et al., 2005). These intersubject variations are typically due to anatomical differences across ears, including properties of the TM, ossicles, middle ear cavities and inner ear load (Voss et al., 2000; Aibara et al., 2001; Rosowski et al., 2012).

Figure 6:
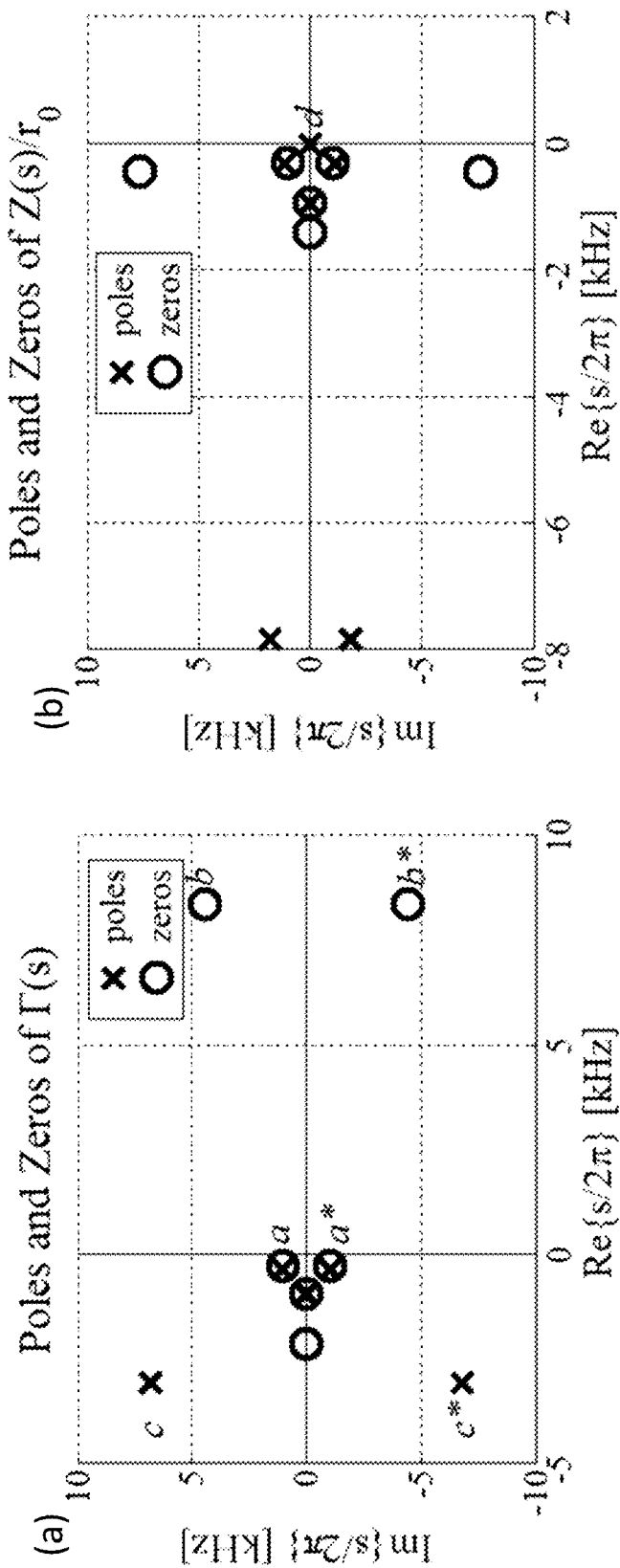
FIG. 6 are plots of the poles and zeros of a CAR pole-zero model.

FIG. 6 shows the poles and zeros that produce the fit to the B&K 4157 shown in FIG. 5. FIG. 6(a) shows the poles and zeros of the reflectance fit $\hat{\Gamma}(s)$ and FIG. 6(b) shows the poles and zeros of the normalized impedance fit $\hat{Z}(s)/r_0$, which have been calculated from the fitted reflectance domain poles via Eq. (1). Notice that in both domains the poles and zeros have complex conjugate symmetry (those in the upper half s-plane mirror those in the lower half s-plane); this is a necessary condition for the polynomial coefficients in Eq. (4) to be real. With relation to the magnitude and phase response, the ω=Im(s) location of a pole or zero typically determines the frequency region in which it has the largest effect, and the σ=Re(s) component of a pole or zero is related to the damping. Poles and zeros with smaller damping, which lie closer to the ω axis, have a larger effect on the fitted magnitude and phase responses. Throughout the pending disclosure, pole-zero locations are plotted as s/(2π), such that the frequency axis in Hz f=ω/(2π) may be referenced to the frequency axes of the magnitude and phase responses.

Considering the poles and zeros of $\hat{\Gamma}(s)$ FIG. 6(a), the pole-zero pair labeled a (with conjugate a*) seems to characterize the first minimum of the magnitude reflectance at 1 [kHz] (FIG. 5(a)), while the zero at b (b*) and the pole at c (c*) correspond to its high frequency behavior. Considering the pole-zero plot of the normalized impedance $\hat{Z}(s)/r_0$ (FIG. 6(b)), note the solitary pole, labeled d, on the real axis approximately at the origin. This pole is actually in the right half s-plane (RHP), with a relatively small value of σ/(2π)=9 [Hz], causing the impedance fit to be unstable. Because its |σ| value is small, pole d is functionally at the origin; such small instabilities in the impedance can occur when fitting reflectance domain data. Because it is approximately at the origin, the pole at d characterizes the stiffness of the impedance below 1 [kHz]; it has a stronger effect on $|\hat{Z}(j\omega)|/r_0$ (FIG. 5(b)) than the other zeros and poles on the real axis, as it has the smallest s value. Thus, the pole-zero fits may be used to model some physics of CAR and impedance measurements.

It is important to note that pole-zero fitting of CAR data cannot be accomplished by autoregressive moving-average (ARMA) modeling methods (e.g. Recio-Spinoso et al., 2011), because the time domain signal $\gamma(t)=F^{-1}\{\Gamma(\omega)\}$ (where $F^{-1}$ denotes the inverse Fourier transform). CAR is measured as a function of frequency, and measurement noise below 100 or 200 [Hz] typically prevents the accurate calculation of an inverse FFT. Instead, a method developed by Gustaysen and Semlyen (1999) is used to fit CAR data directly in the frequency domain. This procedure finds a rational approximation of the data as a function of complex frequency, using their 'vector fitting' method. Such pole zero fits capture magnitude and phase characteristics of CAR measurements with low RMS relative error and a small set of parameters. The fitting procedure is described herein and Robinson 2013 as well as further results and diagnostic implications.

The CAR measurement data sets described herein were compiled from previous studies. A population of normal ears was drawn from Voss and Allen (1994) and Rosowski et al. (2012). Fourteen CAR measurements of ten ears (four retest measurements) were collected in vivo up to 15 [kHz] by Voss and Allen, using a measurement system described therein. The B&K 4157 and DB-100 ear simulator measurements shown in FIG. 5 were also collected in that study. Fifty-eight CAR measurements (and 58 retest measurements) were collected in vivo over a frequency range of 0.2e6 [kHz] by Rosowski et al., using the Mimosa Acoustics HearID system. These 58 "strictly normal" ears met specific audiometric criteria in order to be included in the study. Pathological and cadaver measurements were drawn from Nakajima et al. (2012) and Voss et al. (2012). The Nakajima et al. (2012) CAR measurements were collected in vivo from patients with confirmed stapes fixation due to otosclerosis, ossicular discontinuity, and superior semicircular canal dehiscence. The Voss et al. (2012) CAR measurements were collected from cadaver preparations, which were manipulated to simulate static pressure disorders in the middle ear cavity (positive and negative), middle ear fluid, fixed stapes, disarticulated incudo-stapedial joints, as well as TM perforations. Additionally, the cadaver ears were measured in their 'normal' (unmodified) state. These data were also collected using the Mimosa Acoustics HearID system.

Rational approximations of the CAR data as a function of frequency $\omega=2\pi f$ were calculated using a vector fitting procedure developed by Gustaysen and Semlyen (1999). $\hat{F}(s)$ where $s=\sigma+j\omega$ is the complex angular frequency variable, denotes the complex frequency domain fit, and $F(\omega)$ denotes the measured complex frequency domain data. It is important to note that the data is only available as a function of $\omega$, thus the data is related to the fitted function by $F(\omega)=\hat{F}(s)|_{s=j\omega}$; in words, when $\hat{F}(s)$ is evaluated along the $\omega$ axis of the complex s-plane, it approximates the observed data. Because the middle ear is not a lossless system, the poles and zeros of the fit are typically located off the $\omega$ axis (have non-zero s values related to the damping). Thus $\hat{F}(s)|_{s=j\omega}$ typically has minima and maxima instead of zero and infinite values.

The data (e.g. the complex reflectance $\Gamma(\omega)$, impedance $Z(\omega)$, or admittance $Y(\omega)=1/Z(\omega)$) is fit to a residue expansion of the form $$\hat{F}(s)=\Sigma_{i=1}^{N_p}(C_i)/(s-A_i)+D+Es \qquad (5)$$

where the constants D and E are real quantities, while the constant poles and residues, $A_i$ and $C_i$, are either real or occur in complex conjugate pairs. Note that if E and D are non-zero, the numerator order ($N_z$, Eq. (4)) is one greater than the denominator order ($N_z=N_p+1$). Similarly, if E is zero and D is non-zero the numerator and denominator orders are equal ($N_z=N_p$), and if both D and E are zero the numerator order is one less than the denominator order ($N_z=N_p-1$). Equation (5) is nonlinear in its unknowns, because the unknown poles $A_i$ appear in the denominator. Because the poles and zeros of a 1-port network impedance are restricted to first order, with a relative order of $|N_z-N_p|\leq 1$, the functional form of Eq. (5) is sufficient for fitting impedance domain data (Van Valkenburg, 1964). The reflectance does not have the same constraints, but given its relationship to impedance (Eq. (1)) it is assumed it will also fit well to this form. It is important to note that while the total number of parameters may seem daunting, there are typically fewer 'degrees of freedom' than it seems, because the complex poles and zeros are constrained to come in complex conjugate pairs. For instance, if a fit has twelve poles and ten of them are complex, there are only seven 'degrees of freedom' related to the poles, because five (half) of the complex poles are constrained by conjugate symmetry. This constraint is preserved under the transformation in Eq. (1).

The vector fitting procedure is a two step process, which converts a nonlinear least squares problem to a linear least squares problem by introducing an unknown scaling function with known poles (Gustaysen and Semlyen, 1999). Given a fixed number of poles, the algorithm converges very rapidly, usually within a few iterations. The algorithm may be re-run with an increasing number of poles, until some error criterion is met. For some measurements, the fitting procedure may return a set of poles and zeros with nearly overlapping pole-zero pairs, due to small extrema from measurement noise. Such pairs may be considered to 'overfit' the data, and it is often possible to eliminate them from the fit without causing an appreciable increase in the fitting error. In the pending disclosure, goodness of fit may be described using a mean squared error (MSE) metric, in decibels, relative to the L2 norm of the signal:

$$\text{MSE [dB]}=10\log_{10}[(\Sigma|F(\omega)-\hat{F}(\omega)|^2)/(\Sigma|F(\omega)|^2)] \qquad (6)$$

A MSE of −30 [dB] corresponds to a RMS relative error of about 3%.

Figure 7:
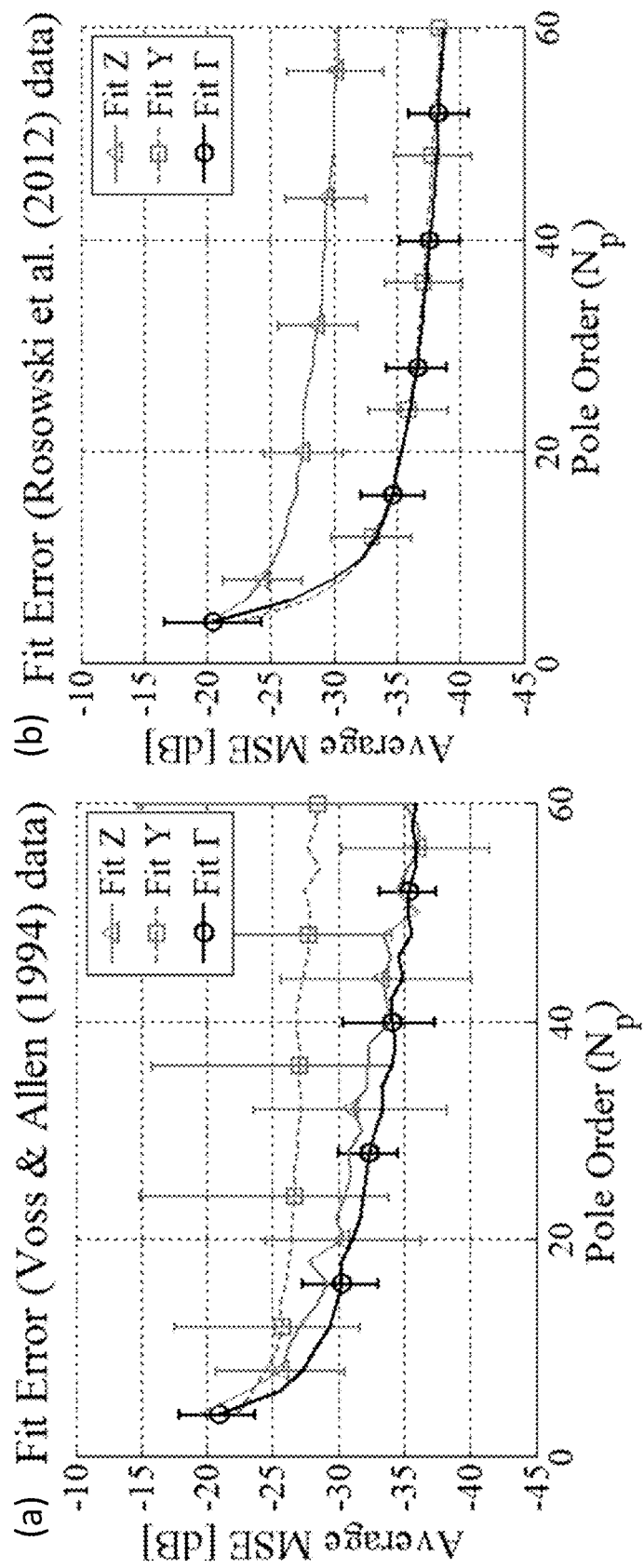
FIG. 7 are plots of the fit error of a CAR pole-zero model.

An error analysis of the fitting procedure is given in FIG. 7. Average MSE vs. pole order is plotted for pole-zero fits of two data sets of normal middle ears in different domains. The impedance (Z), admittance (Y), and reflectance (F) domains are examined. FIG. 7a shows the average MSE for fits of 14 normal ear measurements made by Voss and Allen (1994) over 0.1e10 [kHz]. FIG. 7(b) shows the average MSE for fits of 112 normal ear measurements made by Rosowski et al. (2012) over 0.2-6 [kHz]. Error bars show ±1 standard deviation of the MSE for a given data set and fitting domain. Considering FIGS. 7(a) and (b), the fit error saturates between about 10 and 20 poles, beyond which the algorithm begins to fit the measurement noise; this behavior is best captured by the admittance and reflectance domain curves in FIG. 7(b), where the error improves by 15 [dB] between 4 and 20 poles, and by less than 5 [dB] between 20 and 60 poles. FIG. 7(a) shows higher average MSEs than FIG. 3(b). This is primarily because the Voss and Allen (1994) measurements were fit over a larger frequency range, which includes more noise than the Rosowski et al. (2012) measurement range. In FIG. 7(a), impedance domain fitting performs better than admittance domain fitting, and vice versa in FIG. 7(b), due to the frequency range of the fit and measurement noise. Because of the typical shape of the impedance response (e.g. FIG. 5(b)), low frequency noise has a larger effect on error in the impedance domain, and high frequency noise has a larger effect on error in the admittance domain. There are differing amounts of low and high frequency noise over the 0.1-10 [kHz] and 0.2-6 [kHz] ranges, causing differences in impedance domain error relative to admittance domain error.

Considering FIG. 7, the fitting procedure consistently performs best in the reflectance domain. Additionally, for diagnostic applications it may be desirable to have the best possible fit to the magnitude reflectance, which has shown the greatest promise for detecting middle ear pathologies. While the impedance magnitude and phase are both dominated by the ear canal response, in the reflectance domain only the phase is significantly affected by the ear canal (e.g. Eq. (2)). Additionally, the dynamic range of the reflectance is much smaller than that of the impedance, typically spanning less than 10 [dB], whereas the impedance may span 20-40 [dB] (1-2 orders of magnitude). Due to the nature of the least squares procedure, small magnitude data points of $Z(\omega)$ inadvertently receive less emphasis in the fitting procedure than data points with larger magnitude. Thus, fitting to the impedance may provide a better approximation to the low frequency data (where the magnitude is large, as in FIG. 5(b), but may yield a relatively poorer fit in the mid-frequency region of the reflectance magnitude, where individually varying minima and maxima occur for normal middle ears. To characterize the reflectance for a given ear, it may be useful to capture these fluctuations. Due to the smaller dynamic range of the reflectance, fitting the data in the reflectance domain gives approximately equal weight to the error across frequencies. Fitting 112 measurements over the 0.2-6 [kHz] range in the reflectance domain, an average MSE of −33.4 [dB] (2.1% RMS relative error with a standard deviation of 0.7%) is achieved with 12 poles for 18 iterations of the fitting algorithm. Fitting the data over a larger frequency range typically requires more poles.

Considering all measurements from the Rosowski et al. (2012) and Nakajima et al. (2012) studies, it was found that reflectance domain fits usually yield values of E (Eq. (5)) that are close to zero. Typically, |E| is very small for fits to both normal and pathological CAR measurements, on the order of $10^{-5}$ for fits with $N_p < 20$. For higher pole orders there is more variation in the value of |E|, which is to be expected as the number of fitting parameters increases. Average |E| values are similar for normal and pathological data sets, indicating that this is a property of reflectance measurements and not a property of middle ear functionality. These results suggest that E should be forced to zero when fitting in the reflectance domain, enforcing a relative pole-zero order of $N_p \geq N$. For most fits, forcing E to be zero has a negligible effect on the error; often this effect may be remedied by adding a few more poles. However, the average value of |D| is on the order of 1 for fits with $N_p < 20$. For instance, when fitting 112 measurements of normal ears from Rosowski et al. (2012) with $N_p = N_z = 12$, the average magnitude of D is 0.8 with a standard deviation of 0.4. Thus, it seems necessary to allow D to be non-zero when fitting in the reflectance domain, resulting in a relative pole-zero order of $N_p = N_z$. While it may not be obvious, this is a significant conclusion due to the physical meaning of D, as described herein.

When the fitting procedure is performed in the reflectance domain, all fits to $\Gamma(\omega)$ are stable (all poles are in the left half s-plane (LHP)) because stability is enforced by the vector fitting procedure. However, when the fit is transformed to the impedance domain by the relation in Eq. (1), stability is not ensured. If E is allowed to be non-zero, out of the fits performed to 112 measurements of $\Gamma(\omega)$ over 0.2-6 [kHz] (Rosowski et al., 2012) with a −30 [dB] MSE tolerance, no fits are stable when transformed to the impedance domain. With E forced to zero and all other conditions the same, 59 fits are stable in the impedance domain. All of these fits are also minimum-phase in the impedance domain, meaning that the zeros of $\hat{Z}(s)/r_0$ reside in the LHP as well as the poles, ensuring that both the impedance and admittance are causal and stable. Of the 53 remaining fits to $\Gamma(\omega)$ that are unstable when transformed to the impedance domain, 46 have a single pole of $\hat{Z}(s)/r_0$ that lies on the real axis in the RHP causing the instability; that pole has a mean value of $\sigma/2\pi r = 17.8$ [Hz], with a standard deviation of 12.2 [Hz]. Thus, for these 46 fits, the unstable pole is approximately at the origin of the s-plane, characterizing the low frequency stiffness of $Z(\omega)$ for a normal middle ear. The remaining 7 fits to $\Gamma(\omega)$ which are unstable in the impedance domain have higher pole orders and may need more careful attention during the fitting procedure (e.g. the data is noisy). Note that the impedance should be minimum-phase, and it should also have the positive real property, Re $\{Z(\omega)\} \geq 0$ for $\sigma = \text{Re}(s) > 0$ (RHP s-plane), assuming the system is passive (Brune, 1931). Due to noise, some CAR measurements have $|Z(\omega)| > 1$, corresponding to Re $\{Z(\omega)\} \leq 0$ for some $\omega$ (Van Valkenburg, 1964). Typically, all fits to these measurements may also have $|\hat{\Gamma}(\omega)| > 1$.

Considering the CAR instead of its magnitude re-introduces the problem of comparing across measurements, because the residual ear canal introduces uncontrolled variation in the complex response (due to varying probe-TM distance, and canal area). This effect is difficult to extract, particularly because the limited high frequency range of the measurements does not allow for a good estimate of any pure delay in the ear canal. Even though measurements are available to 15 [kHz] for the Voss and Allen (1994) study, there is high frequency noise in the data that makes it difficult to accurately estimate the distance L from the probe to the TM (this point was previously made in their 1994 publication). Under the assumption that the ear canal is lossless, and the rest of the middle ear system has loss, the reflectance may be factored such that the residual ear canal effect is approximately removed.

Using the Weiner factorization technique $$\hat{\Gamma}(s) = \hat{\Gamma}_{mp}(s)\hat{\Gamma}_{ap}(s) \qquad (7)$$

where $\hat{\Gamma}_{mp}(s)$ is the minimum-phase component and $\hat{\Gamma}_{ap}(s)$ is the all-pass component of the pole-zero fit $\hat{\Gamma}(s)$, it is possible to preserve the magnitude reflectance while removing variable residual canal delay. By definition, it is required that all poles and zeros of a minimum-phase function lie in the LHP. To construct the minimum phase component $\hat{\Gamma}_{mp}(s)$, we must factor a component out of $\hat{\Gamma}(s)$ that accounts for all zeros that lie in the RHP (if the fit was performed in the reflectance domain, all poles will be constrained to the LHP by the vector fitting procedure. Let the function $\hat{\Gamma}_{LHP}(s)$ contain all the poles and zeros of $\hat{\Gamma}(s)$ that lie in the LHP; let $N_{z,RHP}$ be the number of RHP zeros of $\hat{\Gamma}(s)$ with values $q_i$. The reflectance fit may be factored as follows:

$$\hat{\Gamma}(s) = \hat{\Gamma}_{LHP}(s) \prod_{i=1}^{N_{z,RHP}} (s - q_i) \qquad (8)$$

$$= \hat{\Gamma}_{LHP}(s) \prod_{i=1}^{N_{z,RHP}} (s - q_i)[(s + q_i^*)/(s + q_i^*)]$$

$$= [\hat{\Gamma}_{LHP}(s) \prod_{i=1}^{N_z,RHP} (s + q_i^*)][\prod_{i=1}^{N_z,RHP} (s - q_i)/(s + q_i^*)]$$

where $\hat{\Gamma}_{mp}(s)=[\hat{\Gamma}_{LHP}(s)\Pi_{i=1}^{N_{z,RHP}}(s+q^*_i)]$ and $\hat{\Gamma}_{ap}(s)=[\Pi_{i=1}^{N_{z,RHP}}(s-q_i)/(s+q^*_i)]$.

Considering Eq. (8), overlapping poles and zeros are introduced in the LHP at $s=q_i$. Grouping the terms, a component with LHP poles and RHP zeros symmetrically placed about the $\omega$ axis emerges. This is called the all-pass component, because its magnitude $\hat{\Gamma}_{ap}(j\omega)$ is 1 for all frequencies in the fitting range; it passes all frequencies with no attenuation. The factorization required to form the all-pass component is unique. The remaining terms contain only poles and zeros in the LHP, and form the minimum-phase factor $\hat{\Gamma}_{mp}(s)$. When working with poles and zeros, this factorization requires no additional calculations.

Figure 8:
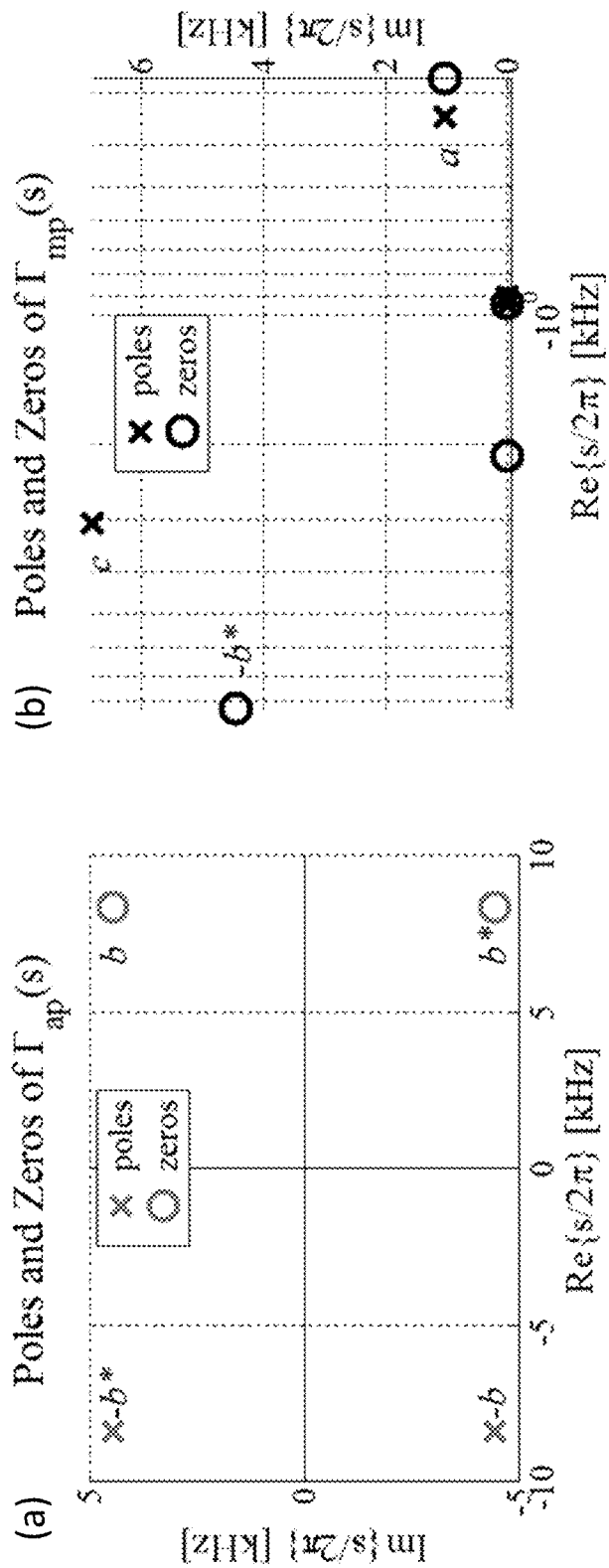
FIG. 8 are plots of the poles and zeros of a CAR model after an example factorization.

An example of this factorization is shown in FIG. 8. FIG. 8(a) shows the all-pass component and FIG. 8(b) shows the minimum-phase component of the reflectance fit shown in FIG. 6(a) (the B&K 4157). Note that FIG. 8(b) shows only the northwest quadrant of the s-plane. This style of plotting may be used for all $\hat{\Gamma}_{mp}(s)$ results; though limited to one quadrant of the LHP, it completely describes the set of poles and zeros for a given fit. By definition, $\hat{\Gamma}_{mp}(s)$ only has poles and zeros in the LHP. Thus, a logarithmic s axis may be used for the LHP (northwest and southwest quadrants), on which the large dynamic range of s values may be more easily viewed. Because the southwest quadrant contains only complex conjugates of the poles and zeros in the northwest quadrant, it does not need to be shown. Considering FIG. 6(a), the zeros at b and b* correspond to the $q_i$'s in Eq. (8). To factor the fit, overlapping poles and zeros are introduced at -b* and -b, respectively; the zeros are assigned to $\hat{\Gamma}_{mp}(s)$ (FIG. 8(b)), and the poles are assigned to $\hat{\Gamma}_{ap}(s)$ (FIG. 8(a)) along with the RHP zeros of $\hat{\Gamma}(s)$. Note how the poles and zeros of $\hat{\Gamma}_{ap}(s)$ are symmetrically placed about the u axis, such that the poles and zeros at b, b*, -b* and -b are constrained by both complex conjugation and all-pass symmetry.

The minimum-phase and all-pass factors have the following properties:

$$|\hat{\Gamma}_{mp}(j\omega)|=|\hat{\Gamma}(j\omega)| \quad (9)$$

$$|\hat{\Gamma}_{ap}(j\omega)|=1 \quad (10)$$

$$\angle(\hat{\Gamma}_{mp}(j\omega))+\angle(\hat{\Gamma}_{ap}))=\angle(\hat{\Gamma}(j\omega)) \quad (11)$$

The reflectance magnitude is maintained in the minimum phase component of the fit, while the component of the reflectance that is uniformly lossless across the frequency range of the fit, including any pure delay, is accounted for in the all-pass component. Because the factors are multiplied, their phases add.

Assuming negligible losses in the ear canal, it can be approximated that the residual ear canal contribution to the reflectance as the all-pass component $\hat{\Gamma}_{ap}(j\omega)$. In some cases, the all-pass component of the factorization has an approximately linear phase (constant group delay), resulting in a robust estimate L' of the ear canal length according to Eq. (2). From this equation, the constant group delay may be calculated as $$\tau_{ap}(\omega)=-d\varphi_{ap}(\omega)/d\omega\sim 2\hat{L}/c \quad (12)$$

where $\varphi_{ap}(\omega)$ is the phase of is $\hat{\Gamma}_{ap}(j\omega)$. If $\tau_{ap}(\omega)$ is frequency dependent, a frequency independent delay may be estimated by taking its minimum over the measured frequency range. When $\hat{\Gamma}_{ap}(s)$ gives a good approximation to the residual ear canal component of the reflectance, $$\hat{\Gamma}_{mp}(s) \sim \hat{\Gamma}_{TM}(s) \quad (13)$$

Thus, from this factorization it is possible to estimate the normalized TM impedance using Eq. (1), $$\hat{Z}_{TM}(s)/r0=(1+\hat{\Gamma}_{mp}(s))/(1-\hat{\Gamma}_{mp}(s)) \quad (14)$$

When the approximate residual ear canal contribution has been removed, the magnitude TM impedance $|\hat{Z}_{TM}(j\omega)|/r0$ typically has no high frequency notch due to ear canal standing waves. In the case of a uniform ear canal area A(x), the TM impedance estimate is similar to the 'propagated impedance' function described by Voss and Allen (1994), calculated by removing a pure delay from the reflectance.

Figure 9:
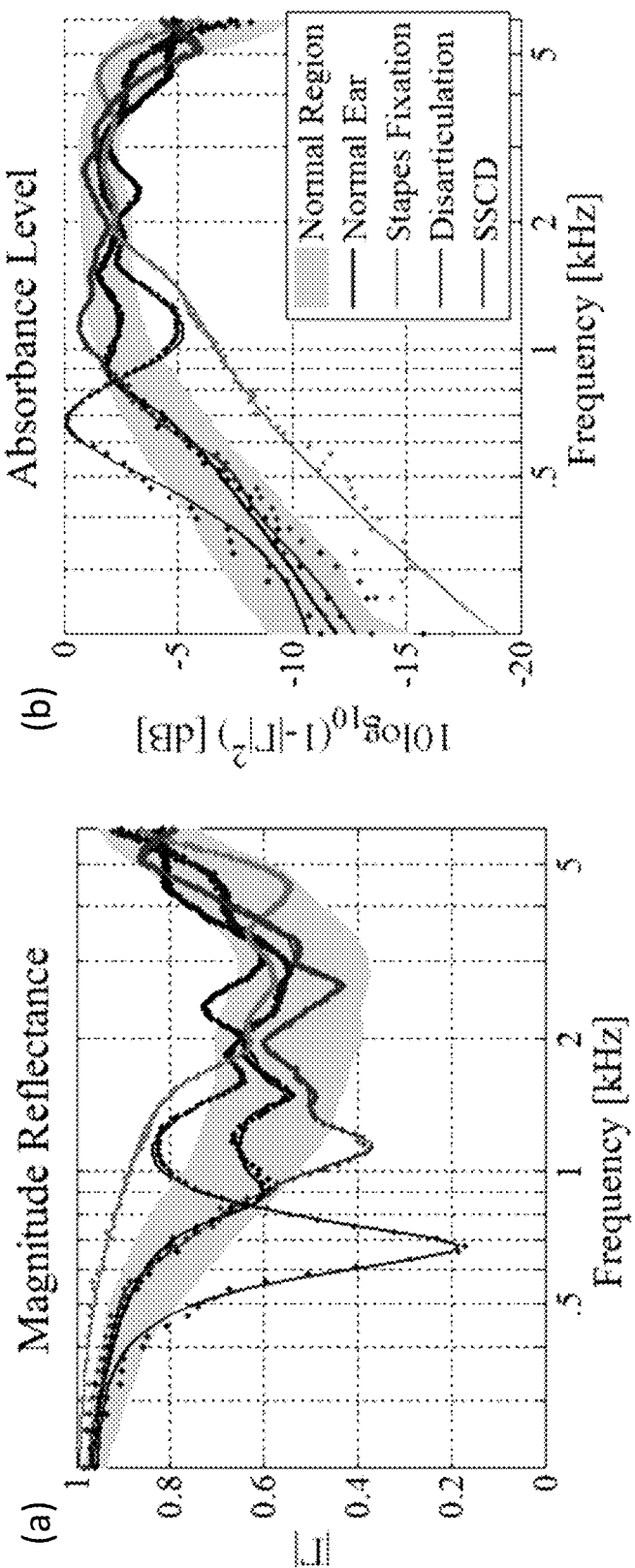
FIG. 9 are plots of the CAR measurement data and pole-zero fits of corresponding CAR pole-zero models of magnitude reflectance and absorbance level for various middle ear conditions.

FIG. 9 shows data and pole-zero fits of four reflectance measurements of ears with varying middle ear conditions (one normal and three pathologies). FIG. 8 shows a reflectance summary. These poles and zeros were chosen to show the effect of pole-zero locations on the magnitude response. Such embodiments show pole-zero fits for various pathologies; two poles, zeros, or pole-zero pairs are chosen for each pathology, but any poles and zeros of the fit could be analyzed in this way.

FIG. 9(b) shows the absorbance level in [dB] (Allen et al., 2005; Rosowski et al., 2012), defined as $$\text{Absorbance [dB]}=10\log_{10}(1-|\Gamma(\omega)|^2) \quad (15)$$

where $1-|\Gamma(\omega)|^2$ is the power absorbance. The mean and normative region of the absorbance level for normal middle ears have a very distinct shape. Rosowski et al. (2012) characterize the rising slope as 15 [dB] per decade and the falling slope as -23 [dB] per decade, with a flat region occurring between about 1 and 4 [kHz]. This is a useful way to characterize reflectance data, because deviations of the absorbance level from normal are more easily recognized, and are closely related to hearing sensitivity (Allen et al., 2005). Additionally, the absorbance level condenses in a rational way the region of individual variation in the magnitude reflectance for normal ears, to a range of a few [dB].

Figure 10:
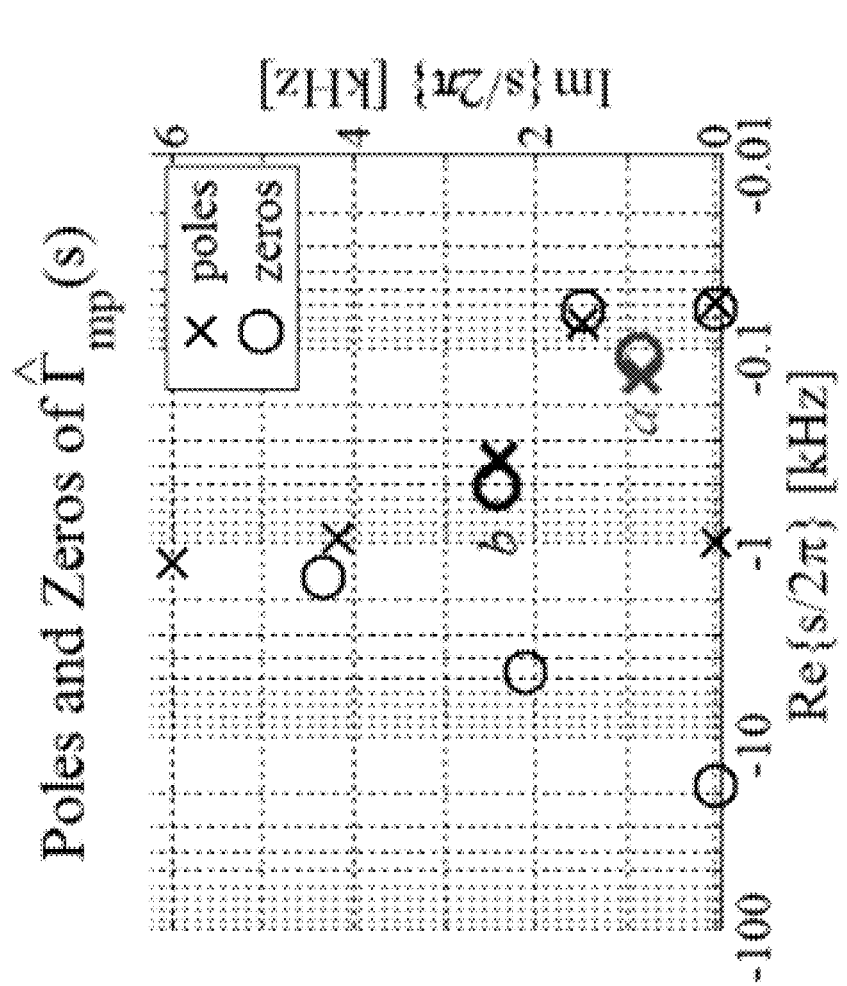
FIGS. 10-13 are pole-zero plots of CAR pole-zero models of the minimum phase component of the reflectance of various middle ear conditions.

Consider the normal ear measurement shown in FIG. 9, ear 22L of the Rosowski et al. (2012) study of normal ears. This fit was performed on reflectance domain data with E forced to zero, achieving a MSE of -35.6 [dB] with 12 poles and 12 zeros. The resulting poles and zeros of $\hat{\Gamma}_{mp}(\omega)$ are shown in FIG. 10. The magnitude reflectance $|\hat{\Gamma}_{mp}(j\omega)|=|\hat{\Gamma}(j\omega)|$ is plotted in FIG. 9(a) (black). Normative data, showing ±1 standard deviation for 112 measurements of normal ears (Rosowski et al., 2012), is plotted as the shaded gray region in FIGS. 9(a) and (b); ear 22L falls within this normal region.

Thus, the individually varying fine-structure minima and maxima in the 1-5 [kHz] range (Allen et al., 2005; Rosowski et al., 2012) seem to be characterized primarily by closely-associated pole-zero pairs in that frequency range. Identifying the pole-zero behavior that characterizes the variation of normal ears may allow for better detection of abnormal reflectance measurements. Additionally, the pole-zero pair located close to 1 [kHz] corresponds to the first minimum of $|\hat{\Gamma}(j\omega)|$ and the 'breakpoint' of the power absorbance (FIG. 9(b)), between the low-frequency ramp and the flat region. Based upon the pole-zero fits for this ear, the B&K 4157 (FIG. 8(b)), Voss and Allen (1994) subject #7 (FIG. 5(b)), and Voss et al. (2012) cadaver ear 12R, it seems that $|\hat{\Gamma}_{mp}(j\omega)|$ for normal ears may typically have pole-zero pair near 1 [kHz], characterizing the breakpoint of the absorbance level (and the first minimum of the magnitude reflectance).

Figure 11:
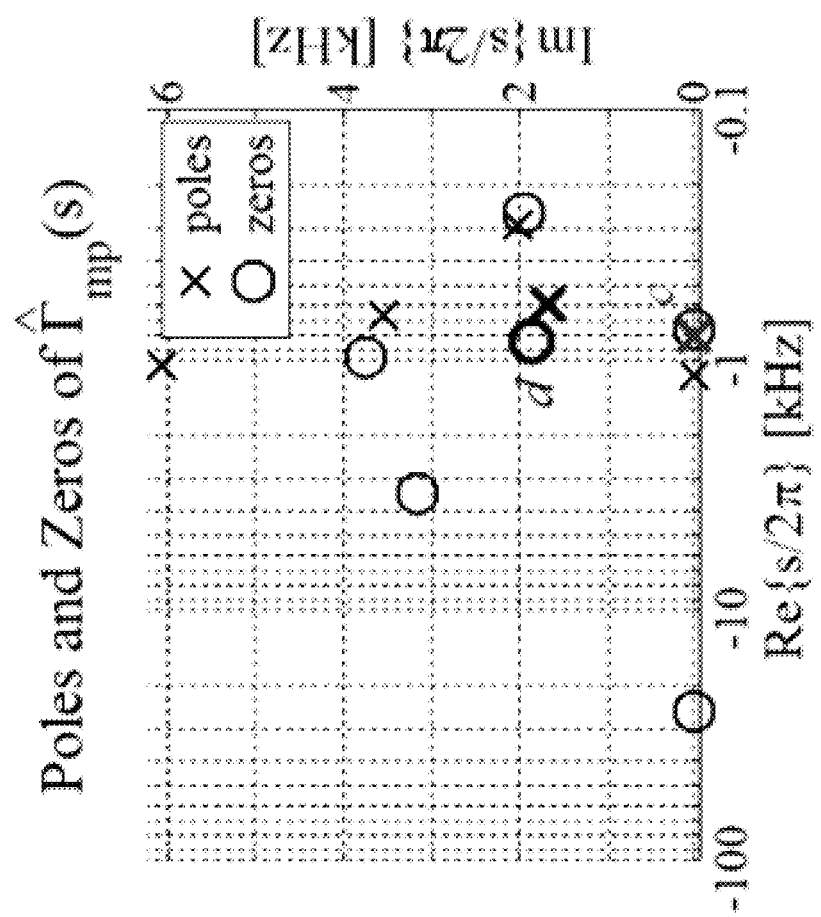

The orange fit curve and data points in FIGS. 9(a) and (b) show an example CAR measurement (patient ear 62L, Nakajima et al. (2012)) for a patient with a pathology that is confirmed stapes fixation due to otosclerosis, in the presence of an intact TM and aerated middle ear. The reflectance domain fit has Np=10, Nz=10, and a MSE of −40.3 [dB]. The absorbance level (FIG. 9(b)) and magnitude reflectance (FIG. 9(a)) for this ear fall significantly outside of the normative regions. Stapes fixation due to otosclerosis is best characterized by an increased middle ear stiffness (Feeney et al., 2003; Allen et al., 2005; Nakajima et al., 2012). This typically results in an elevated reflectance magnitude at low frequencies, corresponding to a right shift of the low-frequency sloping region of the absorbance level (Allen et al., 2005). This behavior is apparent in FIG. 9(b), where the absorbance level curve for ear 62L is significantly shifted to the right of the normative region below 2 [kHz]. The sensitivity plot in FIG. 11 shows a pole c. This pole was chosen because it has the least damping, thus the strongest effect on the reflectance, and the magnitude reflectance is higher (has a more pole-like behavior) at low frequencies. The movement of this pole affects the magnitude reflectance at low frequencies up to about 2 [kHz]. Moving this pole towards the origin strengthens its effect, increasing the magnitude reflectance at low frequencies, and moving it away from the origin may decrease the magnitude reflectance at low frequencies. FIG. 11 shows pole pair d at about 1.75 [kHz]. This pair was chosen because it is the first pole, zero, or pair occurring in frequency off the s axis, when it would be expected to see a pole-zero pair at about 1 [kHz] for a normal ear. While its largest effect occurs in the frequency neighborhood where the pair resides, movement of this pole-zero pair also affects the magnitude reflectance at low frequencies. This pair appears to characterize the breakpoint of the absorbance level (and perhaps also, in part, its slope) for this pathological ear. For normal ears, this breakpoint occurs significantly lower in frequency, around 1 [kHz]

The purple fit curve and data points in FIGS. 9(a) and (b) show an example CAR measurement (patient ear 28L, Nakajima et al. (2012)) for a patient with confirmed ossicular discontinuity, in the presence of an intact TM and aerated middle ear. The reflectance domain fit has $N_p$=10, $N_z$=10, and a MSE of −31.3 [dB]. The absorbance level (FIG. 9(b)) and magnitude reflectance (FIG. 9(a)) for this ear also fall outside the normative regions, but the nature of this variation is quite different from that due to stapes fixation. Ossicular discontinuity typically causes a narrow-band (tuned) resonance in the magnitude reflectance between 0.5 and 0.8 [kHz] (Nakajima et al., 2012). This is visible in the case of ear 28L, which has a deep notch in the reflectance magnitude at about 700 [Hz] and a corresponding elevated absorbance level in that frequency region. The absorbance level does not have a normal breakpoint at 1 [kHz]. The poles and zeros of $\hat{\Gamma}_{mp}(j\omega)$ correspondingly show an abnormal behavior in this range. In this case of ossicular discontinuity there are poles and zeros near 1 [kHz], but they are not tightly paired. Hence, the pole and zero closest in frequency to 1 [kHz] are analyzed.

Figure 12:
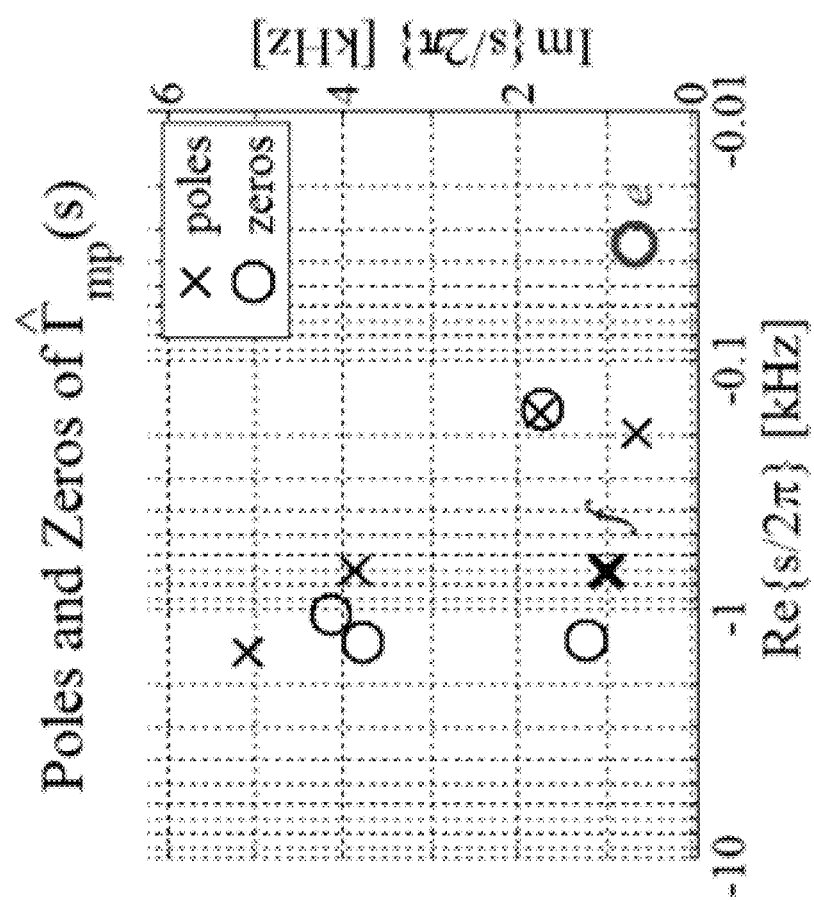

FIG. 12 shows pole e near 700 [Hz] characterizes the deep notch in the magnitude reflectance. The magnitude reflectance is very sensitive to the location of this zero, experiencing sharp relative dips when it is moved higher or lower in frequency. It makes sense that this zero has a large effect on the magnitude response, because it has a very small σ value compared to the other poles and zeros of $\hat{\Gamma}_{mp}(j\omega)$. FIG. 12 also show the pole labeled f at 1 [kHz]. Not only does this pole affect the magnitude reflectance in the 1 [kHz] region (where the magnitude reflectance is higher than average), but it has a significant effect on the magnitude reflectance for all frequencies below 2 [kHz].

The green fit curve and data points in FIGS. 9(a) and (b) show an example CAR measurement (patient ear 52L, Nakajima et al. (2012)) for a patient with confirmed superior semicircular canal dehiscence (SSCD), in the presence of an intact TM and aerated middle ear. The reflectance domain fit has $N_p$=12, Nz=12, and an MSE of −34.3 [dB]. The absorbance level (FIG. 9(b)) and magnitude reflectance (FIG. 9(a)) for this ear fall slightly outside of the normative regions around 1 [kHz]. SSCD typically shows a similar variation from normal to that caused by ossicular discontinuity, though not as extreme (Nakajima et al., 2012). In FIG. 9(a) there is an abnormally deep minimum in the magnitude reflectance at 1 [kHz], corresponding to a slight elevation of the absorbance level at that frequency (FIG. 9(b)), relative to the normal middle ear region. Comparing this with the purple curve for ossicular discontinuity, the effect is similar but not as pronounced, and the notch occurs in a slightly higher frequency range. Because the variation in the magnitude reflectance is observed at low frequencies around 1 [kHz], the sensitivity of poles and zeros in that region is analyzed.

Figure 13:
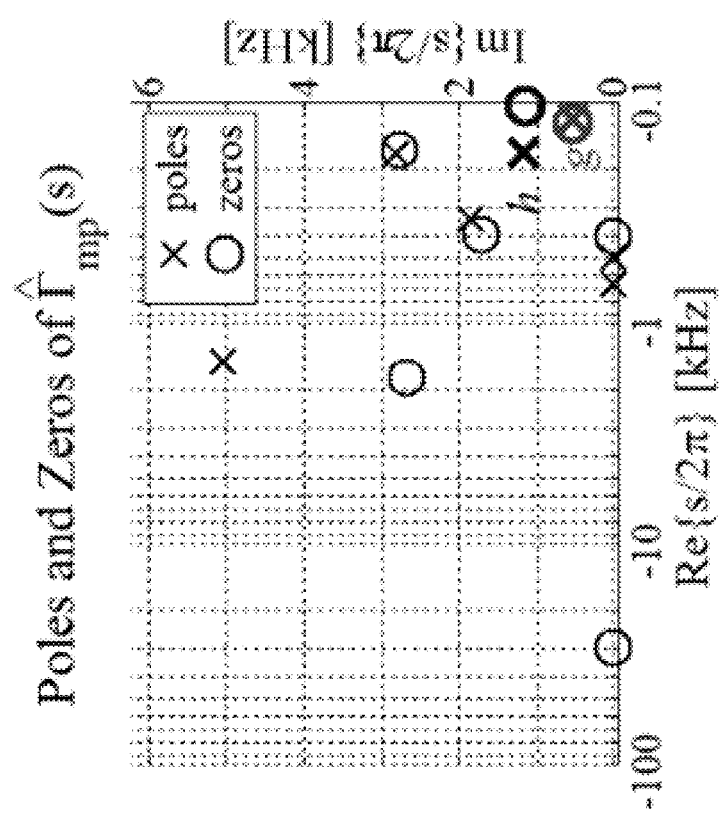

FIG. 13 shows the effect of pole pair g at 500 [Hz] on the magnitude reflectance. This pair was selected because it lies between the σ axis and the normal 1 [kHz] pair location. Shifting this pole-zero pair causes a variation in the reflectance magnitude around that frequency. However, the effect is not very pronounced; the pole and zero are very close together, and appear to be fitting a small noise peak. In fact, this effect is so small compared to the effect of the 1 [kHz] pole-zero pair, that is hard to see. In FIG. 13, the pole-zero pair labeled h at 1 [kHz] causes large variations of the magnitude reflectance in that frequency neighborhood. Notice that the zero of this pair has a significantly smaller σ value than the pole, increasing its relative effect on the reflectance. This zero and its distance from the pole affect the depth of the minimum in the magnitude reflectance at 1 [kHz]. This pole-zero pair also characterizes the nature of the breakpoint in the absorbance level between the initial slope and the flat region. Considering the pole-zero pairs near 1 [kHz] found for normal ears in described herein, the abnormal depth of the 1 [kHz] notch in the SSCD magnitude reflectance could be due to nuances of the location of its 1 [kHz] pair, such as damping and relative distance between the pole and zero.

Systems and methods are described herein for concise parametric characterization of CAR measurements, with the ultimate goal of improving and automating differential diagnosis of middle ear pathology. This is accomplished by fitting poles and zeros to the complex data.

The fitting algorithm is fast, and may be easily implemented in a reflectance measurement system. Ultimately, it should allow for more robust automated classification than visual assessment or correlations between magnitude reflectance values and audiometric measurements. Pole-zero fitting is advantageous because it condenses the entire complex response to a small set of parameters, without extensive processing of the magnitude reflectance (e.g. a somewhat arbitrary choice of the frequency points over which to average the magnitude CAR). However, further study may be performed by using larger volumes of normal and pathological CAR data, in combination with known physical characteristics of normal and pathological middle ears, and the complex data may be further studied, and classification strategies sought.

Pole-zero fits may also be used to synthesize network models of the complex impedance (e.g. Brune (1931)). However, such RLC networks will not necessarily be unique. Networks synthesized from pole-zeros fits of CAR measurements will often lack direct physical interpretations, such as the Zwislocki (1962), Kringlebotn (1988), or Parent and Allen (2010) models. However, they may have utility for analyzing CAR data.

Systems and methods are described herein for examining the physical and mathematical properties of CAR data using pole-zero fitting. Pole-zero fits can characterize CAR data with low error and small number of parameters. While considering the complex data reintroduces the effect of variation in the probe-TM distance, measurements may be effectively compared across ears by factoring the reflectance fit into its minimum-phase and all-pass components. The magnitude of the minimum-phase component of the CAR is equal to the reflectance magnitude, thus preserving the current diagnostic standard. In this preliminary investigation, it was found that pole-zero locations show distinct pole-zero pairs in the mid-frequency region of individual variation for normal ears, and may systematically differ for various pathologies, similar to the magnitude reflectance. Pole-zero modeling enables mathematically characterizing CAR data in order to enable improved automated identification of middle ear pathology using a noninvasive, yet relatively low cost measurement system.

In some embodiments the eardrum impedance, admittance or reflectance may be processed so as to determine whether the plots of such eardrum impedance, admittance or reflectance over frequency match plots of middle ear conditions and pathologies as described herein.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A method, comprising:
  transmitting, by a transducer, an acoustic signal into an ear canal;
  measuring, using a microphone on a first end of the ear canal, a complex cavity pressure based on the transmitted acoustic signal reflected by an ear drum situated at a second, distal end of the ear canal;

calculating, by a computing device, a complex acoustic reflectance (CAR) based on the measured complex cavity pressure;

calculating, using the computing device, a CAR pole-zero model such that a residual error between the calculated CAR pole-zero model and the calculated CAR is less than a threshold;

factoring, by the computing device, the CAR pole-zero model into an all pass component and a minimum phase component;

determining, by the computing device, ear drum impedance by removing the all pass component of the CAR pole-zero model;

displaying, on a user interface, poles and zeros of the minimum phase component of the CAR pole-zero model; and automatically determining a normal hearing status by identifying the presence of distinct pole-zero pairs in a mid-frequency region within a predetermined variation associated with normal ears.

2. The method of claim 1, wherein the transducer is calibrated based on the Norton equivalent parameters of an acoustic source.

3. The method of claim 1, further comprising using Weiner filtering to factor the CAR pole-zero model into the all pass component and the minimum phase component.

4. The method of claim 1, further comprising processing the ear drum impedance to determine one or more middle ear pathologies.

5. The method of claim 1, wherein the complex acoustic reflectance is based on a ratio of a reflected wave pressure to an incident wave pressure.

6. The method of claim 1, wherein calculating a CAR pole-zero model uses a vector fitting procedure.

7. The method of claim 1, further comprising automating differential diagnosis of a middle ear pathology by calculating an absorbance level from the minimum phase component of the CAR pole-zero model and comparing the absorbance level with data for a middle ear pathology.

* * * * *